(12) United States Patent
Iwasa et al.

(10) Patent No.: US 11,502,226 B2
(45) Date of Patent: Nov. 15, 2022

(54) LIGHT EMITTING DEVICE

(71) Applicant: NICHIA CORPORATION, Anan (JP)

(72) Inventors: Makiko Iwasa, Anan (JP); Kazushige Fujio, Tokushima (JP)

(73) Assignee: NICHIA CORPORATION, Anan (JP)

( * ) Notice: Subject to any disclaimer, the term of this patent is extended or adjusted under 35 U.S.C. 154(b) by 179 days.

(21) Appl. No.: 16/983,470

(22) Filed: Aug. 3, 2020

(65) Prior Publication Data
US 2020/0365772 A1 Nov. 19, 2020

Related U.S. Application Data

(63) Continuation of application No. 16/426,918, filed on May 30, 2019, now Pat. No. 10,770,628.

(30) Foreign Application Priority Data

May 31, 2018 (JP) .............................. JP2018-105560
May 21, 2019 (JP) .............................. JP2019-095441

(51) Int. Cl.
*H01L 33/50* (2010.01)
*A61L 2/08* (2006.01)
(Continued)

(52) U.S. Cl.
CPC ............ *H01L 33/504* (2013.01); *A61L 2/084* (2013.01); *H01L 33/507* (2013.01); *H01L 33/56* (2013.01);
(Continued)

(58) Field of Classification Search
None
See application file for complete search history.

(56) References Cited

U.S. PATENT DOCUMENTS 8,581,488 B2  11/2013  Sakuta et al.
8,829,778 B2   9/2014  Sakuta et al.
(Continued)

FOREIGN PATENT DOCUMENTS

JP   2008034188 A   2/2008
JP   2010207278 A   9/2010
(Continued)

OTHER PUBLICATIONS

Chen, L., et al. Light Converting Inorganic Phosphors for While Light-Emitting Diodes, (Mar. 22, 2010), vol. 3, No. 3, Materials, 24 pages.
(Continued)

*Primary Examiner* — Benjamin P Sandvik
(74) *Attorney, Agent, or Firm* — Hunton Andrews Kurth LLP

(57) ABSTRACT

A light emitting device includes a light emitting element having an emission peak wavelength in a range of 380 nm to 420 nm and a fluorescent member including at least one fluorescent material that is excited by light from the light emitting element for light emission, wherein a mixture of light from the light emitting element and light from the fluorescent material has a correlated color temperature in a range of 2000 K to 7500 K as measured according to JIS Z8725, and the light emitting device has a spectral distribution in which, when the integral value over a wavelength range of 380 nm to 780 nm is normalized to 100%, the proportion of an integral value over a wavelength range of 380 nm to 420 nm is 15% or more, and the ratio a as defined by the expression (1) is 0.9 or more and 1.6 or less.

14 Claims, 24 Drawing Sheets

(51) Int. Cl.
  *H01L 33/56* (2010.01)
  *H01L 33/60* (2010.01)
  *H01L 33/32* (2010.01)
  *H01L 33/48* (2010.01)
  *H01L 33/62* (2010.01)

(52) U.S. Cl.
  CPC ........... *H01L 33/60* (2013.01); *A61L 2202/11* (2013.01); *H01L 33/32* (2013.01); *H01L 33/486* (2013.01); *H01L 33/62* (2013.01)

(56) References Cited

U.S. PATENT DOCUMENTS

| | | |
|---|---|---|
| 8,829,780 B2 | 9/2014 | Sakuta et al. |
| 2012/0112626 A1 | 5/2012 | Sakuta et al. |
| 2012/0319565 A1 | 12/2012 | Sakuta et al. |
| 2014/0021493 A1* | 1/2014 | Andrews ................ H01L 33/60 257/E33.068 |
| 2014/0042896 A1 | 2/2014 | Sakuta et al. |
| 2015/0131043 A1 | 5/2015 | Yamamoto et al. |
| 2015/0380460 A1 | 12/2015 | Horie |
| 2017/0005239 A1* | 1/2017 | Asai ................ C09K 11/7734 |
| 2017/0030555 A1 | 2/2017 | Lalicki et al. |
| 2017/0256684 A1 | 9/2017 | Asai |
| 2017/0309795 A1* | 10/2017 | Kim ................ C09K 11/0883 |
| 2017/0368210 A1* | 12/2017 | David ................ H05B 33/14 |
| 2018/0076181 A1 | 3/2018 | Onuma et al. |
| 2018/0351050 A1 | 12/2018 | Yamakawa et al. |
| 2019/0371978 A1 | 12/2019 | Iwasa et al. |
| 2021/0043809 A1* | 2/2021 | Katou ................ H01L 33/54 |

FOREIGN PATENT DOCUMENTS

| | | |
|---|---|---|
| JP | 2011071404 A | 4/2011 |
| JP | 2011159769 A | 8/2011 |
| JP | 2011159832 A | 8/2011 |
| JP | 2012056970 A | 3/2012 |
| JP | 2012060097 A | 3/2012 |
| JP | 2013045896 A | 3/2013 |
| WO | 2017135255 A1 | 8/2017 |

OTHER PUBLICATIONS

Smet, P., et al. Selecting Conversion Phosphors for While Light-Emitting Diodes, (Jan. 1, 2011), vol. 158, No. 6, Journal of the Electrochemical Society, 18 pages.

* cited by examiner

LIGHT EMITTING DEVICE

CROSS-REFERENCE TO RELATED PATENT APPLICATION

This is a continuation application of U.S. patent application Ser. No. 16/426,918, filed May 30, 2019, which claims priority to Japanese Patent Application No. 2018-105560, filed on May 31, 2018, and Japanese Patent Application No. 2019-95441, filed on May 21, 2019, the entire disclosures of which are incorporated herein by references in their entirety.

BACKGROUND

Technical Field

The present invention relates to a light emitting device.

Description of Related Art

A light emitting device is known that uses, as a light emitting element such as a light emitting diode (hereinafter this may also be referred to as "LED"), a light emitting element that emits a blue color, and uses a fluorescent material that emits a yellow color as excited by the light from the light emitting element, emitting a white mixed color light. Such a light emitting device may have a strong emission intensity in a human visible light range of 380 nm to 780 nm and have a high emission efficiency, but could not have a sufficient emission intensity in a blue green region and a red region as the case may be. Consequently, there is room for improvement for the visibility of irradiated substances (hereinafter this may be referred to as "color rendering property").

Here, for an evaluation process for the color rendering property of a light source, JIS Z8726 stipulates that test colors each having predetermined reflectance characteristics (R1 to R15) are colorimetrically measured with a test light source and a reference light source, and the color difference $\Delta E_i$ (i is an integer of 1 to 15) is numerically calculated to give a color rendering index. The upper limit of the color rendering index Ri (i is an integer of 1 to 15) is 100. Namely, when a color difference between the test light source and the reference light source having a color temperature corresponding is smaller, the color rendering index is higher to come closer to 100. An average value of R1 to R8 among the color rendering indices is referred to as a general color rendering index (hereinafter this may be expressed as Ra), and R9 to R15 are referred to as specialty color rendering indices. Regarding the specialty color rendering indices, it is said that R9 is for a red color, R10 is for a yellow color, R11 is for a green color, R12 is for a blue color, R13 is for a color of Western skin, R14 is a color of tree leaves, and R15 is a color of Japanese skin. For enhancing a color rendering property, for example, Japanese Unexamined Patent Publication No. 2008-34188 discloses a light emitting device that uses a red emitting fluorescent material in addition to a green to yellow emitting fluorescent material.

Depending on the site where it is used, a light emitting device may be often desired to emit a light having a germicidal effect and to exhibit a sterilization effect of reducing the number of germs in the use environments. For example, it is generally known that the optical absorption spectrum of DNA (deoxyribonucleic acid) of germs has an absorption band at around a wavelength of 260 nm, and UV emission at 300 nm or less has a germicidal effect. However, it is also known that UV rays at 300 nm or less have some influences on human and animal DNAs. It is known that in some kinds of germs, the number of germs may be reduced by a violet region light falling within a wavelength range of 380 nm to 420 nm that is a visible range, and the visible light could have a sterilization effect. The influence of the visible light on humans and animals is lower than that of the UV region light having a wavelength range of 300 nm or less, that is, the visible light is safe, and consequently, using a light falling within a wavelength range of 380 nm to 420 nm, an attempt to suppress growth of germs is being made.

For example, Japanese Unexamined Patent Publication No. 2010-207278 discloses a surface sterilization method including irradiation with a light (near-UV light) having a maximum light intensity in a wavelength range of 400 nm to 410 nm for sterilization without having any negative influence on human bodies.

SUMMARY

However, in the case where a light emitting element capable of emitting a light falling within a wavelength range of 380 nm to 420 nm that has a sterilization effect is used, the emission intensity in a violet region is large, as compared with a light emitting element having an emission peak wavelength at around 450 nm and used, for example, in a light emitting device that emits a white mixed color light, and accordingly, the case could not provide a sufficient emission intensity in a blue region and further improvement for the color rendering property is needed.

Given the situation, one embodiment of the present invention is to provide a light emitting device having a sterilization effect and having a high-quality color rendering property for comfortable use even in human visual environments.

The present disclosure includes the following embodiment.

One embodiment of the present disclosure is directed to a light emitting device including: a light emitting element having an emission peak wavelength in a range of 380 nm to 420 nm; and a fluorescent member including at least one fluorescent material that is excited by light from the light emitting element for light emission, a mixture of light from the light emitting element and light from the fluorescent material having a correlated color temperature of 2000 K to 7500 K as measured according to JIS Z8725, the light emitting device having a spectral distribution in which, when an integral value over a wavelength range of 380 nm to 780 nm is normalized to 100%, the proportion of an integral value over a wavelength range of 380 nm to 420 nm is 15% or more, and the ratio a as defined by the following expression (1) falling within a range of 0.9 to 1.6.

$$\text{Ratio } a = \frac{G_L/B_L}{G_S/B_S} \quad (1)$$

In the expression (1), $B_S$ represents a maximum emission intensity in a wavelength range of 430 nm to less than 485 nm in a spectral distribution of a reference light source at the correlated color temperature of the light emitting device, $G_S$ represents a maximum emission intensity in a wavelength range of 485 nm to 548 nm in the spectral distribution of the reference light source at the correlated color temperature of the light emitting device, and the denominator of the expression (1) is a ratio of $G_S$ to $B_S$. In the expression (1), $B_L$ represents a maximum emission intensity in a wavelength range of 430 nm to less than 485 nm in the spectral distribution of the light emitting device, $G_L$ represents a maximum emission intensity in a wavelength range of 485 nm to 548 nm in the spectral distribution of the light emitting device, and the numerator of the expression (1) is a ratio of $G_L$ to $B_L$.

According to the present disclosure, there can be provided a light emitting device having a sterilization effect and having a high-quality color rendering property for comfortable use even in human visual environments.

DETAILED DESCRIPTION

Hereinafter the light emitting device of the present disclosure is described on the basis of one embodiment. The embodiment described below is an exemplification for embodying the technical idea of the present invention, and the present invention is not limited to the light emitting device described below. The relationship between the color name and the chromaticity coordinate, and the relationship between the wavelength range of light and the name of monochromatic light are in accordance with JIS Z8110.

The light emitting device is provided with a light emitting element having an emission peak wavelength in a range of 380 nm to 420 nm, and a fluorescent member including at least one fluorescent material that is excited by the light from the light emitting element for light emission, wherein the correlated color temperature, as measured according to JIS Z8725, of the mixed light of the light of the light emitting element and the light of the fluorescent material is in a range of 2000 K or more and 7500 K or less, and in the spectral distribution of the light emitting device, when the integral value in a wavelength range of 380 nm to 780 nm is normalized to 100%, the proportion of the integral value in a wavelength range of 380 nm to 420 nm is 15% or more, and the ratio a as defined by the following expression (1) falls within a range of 0.9 to 1.6.

$$\text{Ratio } a = \frac{G_L/B_L}{G_S/B_S} \quad (1)$$

In the expression (1), $B_S$ represents a maximum emission intensity in a wavelength range of 430 nm to less than 485 nm in a spectral distribution of a reference light source at the correlated color temperature of the light emitting device, $G_S$ represents a maximum emission intensity in a wavelength range of 485 nm to 548 nm in the spectral distribution of a reference light source at the correlated color temperature of the light emitting device, and the denominator of the expression (1) is a ratio of $G_S$ to $B_S$, $G_S/B_S$. In the expression (1), $B_L$ represents a maximum emission intensity in a wavelength range of 430 nm to less than 485 nm in a spectral distribution of the light emitting device, $G_L$ represents a maximum emission intensity in a wavelength range of 485 nm to 548 nm in the spectral distribution of the light emitting device, and the numerator of the expression (1) is a ratio of $G_L$ to $B_L$, $G_L/B_L$.

Figure 1:
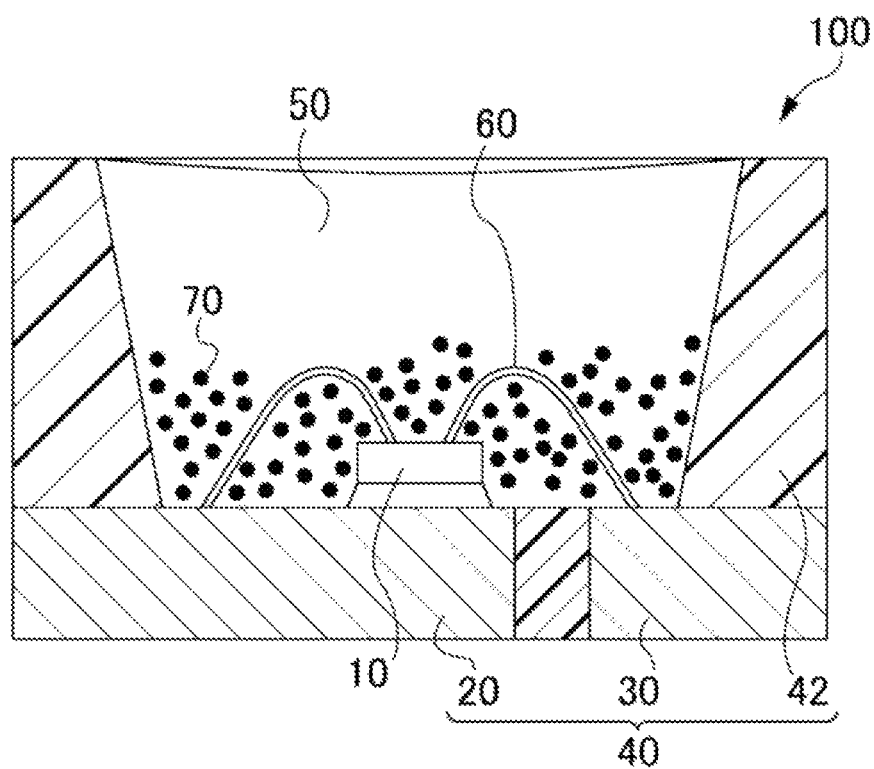
FIG. 1 is a schematic cross-sectional view showing an example of a light emitting device.

One example of the light emitting device of one embodiment of the present disclosure is described with reference to the drawings. FIG. 1 is a schematic cross-sectional view showing a light emitting device 100.

As shown in FIG. 1, the light emitting device 100 is provided with a light emitting element 10 having an emission peak wavelength within a range of 380 nm to 420 nm, and a fluorescent member 50 including at least one fluorescent material 70 that is excited by the light from the light emitting element 10 for light emission.

The light emitting device 100 is, for example, provided with a molded body 40, the light emitting element 10 and the fluorescent member 50. The molded body 40 is formed of a first lead 20, a second lead 30 and a resin part 42 containing a thermoplastic resin or a thermosetting resin that are integrally molded. The molded body 40 forms a concave portion having a bottom and a side wall, in which the light emitting element 10 is mounted on the bottom of the concave portion. The light emitting element 10 has a pair of positive and negative electrodes, and the pair of positive and negative electrodes each are electrically connected to the first lead 20 and the second lead 30, respectively, via a wire 60. The light emitting element 10 is covered by the fluorescent member 50. The fluorescent member 50 includes a fluorescent material 70, which changes the wavelength of the light from the light emitting element 10, and a sealing material. The fluorescent material 70 has at least one emission peak wavelength in a specific wavelength range, as excited by the light from the light emitting element, and may include two or more kinds of fluorescent materials differing in the wavelength range of the emission peak wavelength. The first lead 20 and the second lead 30 electrically connected to the pair of positive and negative electrodes of the light emitting element 10 are partly exposed out toward the outside of the package constituting the light emitting device 100. Via these first lead 20 and second lead 30, the light emitting device 100 receives external power supply for light emission.

Preferably, the fluorescent member 50 for use in the light emitting device includes the fluorescent material 70 and a sealing material. The sealing material may be a resin selected from a thermoplastic resin and a thermosetting resin. In consideration of easy producibility, examples of the resin for use as the sealing material include a silicone resin and an epoxy resin. The fluorescent member may contain any other component such as a filler, a light stabilizer and a colorant, in addition to the fluorescent material 70 and the sealing material. Examples of the filler include silica, barium titanate, titanium oxide and aluminum oxide. The content of the other component than the fluorescent material and the sealing material in the fluorescent member can be set in a preferred range based on the size, the correlated color temperature and the color tone of the targeted light emitting device. For example, the content of the other component than the fluorescent material and the sealing material in the fluorescent member may be 0.01 parts by mass or more and 20 parts by mass or less relative to 100 parts by mass of the sealing material.

The light emitting element 10 is used as an excitation light source. The light emitting element 10 has an emission peak wavelength within a range of 380 nm to 420 nm. The range of the emission peak wavelength of the light emitting element 10 is preferably within a range of 385 nm or more and 415 nm or less, more preferably within a range of 390 nm or more and 410 nm or less, even more preferably within a range of 400 nm or more and 410 nm or less. When the light emitting element 10 has an emission peak wavelength within a range of 380 nm to 420 nm, there can be provided a light emitting device capable of emitting light that falls within a wavelength range having a germicidal effect against bacteria in an environmental atmosphere and capable of reducing the number of bacteria in an environmental atmosphere and thus having a sterilization effect. In this description, "sterilization" means bacterial killing of killing bacteria in a targeted environmental atmosphere to reduce the number of bacteria. The full width at half maximum of the emission spectrum of the light emitting element 10 may be, for example, 30 nm or less, or 25 nm or less, or 20 nm or less. The full width at half maximum means a full width at half maximum (FWHM) of an emission peak of an emission spectrum, and means a wavelength width of an emission peak that indicates a value of 50% of the maximum value of an emission peak in each emission spectrum. The light emitting element 10 is, for example, preferably a semiconductor light emitting element using a nitride-based semiconductor ($In_xAl_yGa_{1-X-Y}N$, $0 \leq X$, $0 \leq Y$, $X+Y \leq 1$). Using a semiconductor light emitting element as the light emitting element, a stable light emitting device having high efficiency and high linearity relative to input and resistant to high mechanical impact can be obtained. A light emitting element having an emission peak wavelength in a range of less than 380 nm could have a high germicidal effect, but has some influences on humans and animals and lowers a color rendering property, and is unfavorable. A light emitting element having an emission peak wavelength in a range of more than 420 nm has a poor germicidal effect and a poor sterilization effect, and is unfavorable.

The correlated color temperature of the mixed light of the light emitted from the light emitting element and the light of the fluorescent material in the light emitting device is, as measured according to JIS Z8725, within a range of 2000 K to 7500 K. Regarding the relationship between the light source color and the range of the correlated color temperature of a light emitting device, JIS Z9112 defines that within a range of 2600 K to 3250 K is a light bulb color, a range of 3250 K to 3800 K is a warm white color, within a range of 3800 K to 4500 K is a white color, within a range of 4600 K to 5500 K is a natural white color, within a range of 5700 K to 7100 K is a daylight color. A light emitting device having a correlated color temperature falling within a range of 2000 K to 7500 K can be a light emitting device capable of emitting a light of a light source color that covers a light bulb color, a warm white color, a white color, a natural white color, and a daylight color. The correlated color temperature of the mixed light from the light emitting device may fall within a range of 2700 K to 7000 K, or may be within a range of 2700 K to 6500 K.

In the spectral distribution of the light emitting device, when the integral value over a wavelength range of 380 nm to 780 nm is normalized to 100%, the proportion of the integral value over a wavelength range of 380 nm to 420 nm is 15% or more. In the spectral distribution of the light emitting device, the case where the proportion of the integral value over a wavelength range of 380 nm to 420 nm is 15% or more relative to the integral value over a range of 380 nm to 780 nm normalized to 100% means that, among the mixed light from the light emitting device, the proportion of the light component falling within a wavelength range that has a germicidal effect can be 15% or more, and accordingly, the light emitting device of the type can have an increased sterilization effect. Among the mixed light from the light emitting device, a larger amount of the light component falling within a wavelength range having a germicidal effect is effective for sterilization, but when the light component falling within a wavelength range having a germicidal effect is too much, emission of light departing from the peak of a human standard relative luminosity (general spectral luminous efficiency) becomes great to lower the emission efficiency. In the spectral distribution of the light emitting device, the proportion of the integral value over a wavelength range of 380 nm to 420 nm relative to the integral value, 100%, over a wavelength range of 380 nm to 780 nm is, from the viewpoint of the sterilization effect of the device, preferably 16% or more, more preferably 17% or more, and is, from the viewpoint of the emission efficiency, preferably 50% or less, more preferably 40% or less, even more preferably 35% or less, and further more preferably 30% or less. Hereinunder in the spectral distribution of the light emitting device in the present description, the integral value over a wavelength range of 380 nm to 420 nm may be expressed as "380 nm to 420 nm emission amount", and the integral value over a wavelength of 380 nm or more and 780 nm or less may be expressed as "total emission amount".

In the light emitting device, the ratio a defined by the expression (1) is within a range of 0.9 or more and 1.6 or less. The ratio a defined by the expression (1) is a ratio of the ratio $G_L/B_L$ as a numerator where $G_L$ is a maximum emission intensity of a green light in a wavelength range of 485 nm to 548 nm in the spectral distribution of the light emitting device and $B_L$ is a maximum emission intensity of a blue light in a wavelength range of 430 m to less than 485 nm in the spectral distribution of the light emitting device, to the ratio $G_S/B_S$ as a denominator where $G_S$ is a maximum emission intensity of a green light in a wavelength range of 485 nm to 548 nm in the spectral distribution of a reference light source at the correlated color temperature of the light emitting device and $B_S$ is a maximum emission intensity of a blue light in a wavelength range of 430 nm to less than 485 nm in the spectral distribution of a reference light source at the correlated color temperature of the light emitting device. When the ratio a defined by the expression (1) for the light emitting device falls within a range of 0.9 to 1.6, the proportion of the green color component relative to the blue color component of the mixed light from the light emitting device is nearly the same as the proportion of the green color component relative to the blue color component in the light emitted from the reference light source, or the light emitting device emits mixed light supplemented with a green color component. When the ratio a defined by the expression (1) for the light emitting device falls within a range of 0.9 to 1.6, the light emitting device can have a sterilization effect and can have an enhanced color rendering property. In the case where the correlated color temperature of the mixed light from the light emitting device is within a range of 2000 K or more and less than 4000 K, the ratio a defined by the expression (1) of the mixed light from the light emitting device is, from the viewpoint of the sterilization effect and the color rendering property of the device, preferably within a range of 1.0 or more and 1.6 or less, more preferably within a range of 1.1 or more and 1.6 or less. In the case where the correlated color temperature of the mixed light from the light emitting device is within a range of 4000 K or more and 7500 K or less, the ratio a defined by the expression (1) of the mixed light from the light emitting device is, from the viewpoint of the sterilization effect and the color rendering property of the device, preferably within a range of 1.0 or more and 1.5 or less, even more preferably 1.1 or more and even more preferably 1.5 or less. JIS Z8726 says that, for a reference light, in principle, a complete radiator is used when the correlated color temperature of the sample light source is less than 5000 K, and when the correlated color temperature of the sample light source is 5000 K or more, in principle, CIE (Commission International de l' Eclairage) daylight is used. In this description, the reference light source conforms to the reference light prescribed in JIS Z8726.

An absolute value A of a value calculated by subtracting the ratio a defined by the expression (1), from 1 is preferably 0.6 or less. Here, the absolute value A of a value calculated by subtracting the ratio a from 1 is an absolute value A of a value calculated by subtracting the ratio a from 1 in the case where the ratio $G_S/B_S$ in the spectral distribution of the reference light source at the correlated color temperature of the light emitting device is the same as the ratio $G_L/B_L$ in the spectral distribution of the mixed light from the light emitting device and where the ratio of the two is 1. When the absolute value A of a value calculated by subtracting the ratio a from 1 is nearer to that of the reference light source at the correlated color temperature of the light emitting device, the light emitting device can emit mixed light well balanced in the blue color component and the green color component therein. When the absolute value A of a value calculated by subtracting the ratio a from 1 is 0.6 or less, the light emitting device can emit mixed light nearer to the mixed light from the reference light source at the correlated color temperature of the light emitting device and well balanced in the blue color component and the green color component, even though the device emits a light of a blue color component having a germicidal effect. The absolute value A of a value calculated by subtracting the ratio a from 1 may be 0.5 or less, or may be 0.4 or less.

The light emitting device has a general color rendering index Ra of 80 or more. According to the classification of fluorescent lamps and LEDs by chromaticity and color rendering property in JIS Z9112, the color rendering property of LEDs is classified into a normal type and a high color rendering type, and the general color rendering index Ra of high color rendering type LEDs is defined to be 80 or more. According to the guideline of CIE, a preferred general color rendering index Ra depending on the site for use is defined to be 60 or more and less than 80 in factories for ordinary works, to be 80 or more and less than 90 in houses, hotels, restaurants, shops, offices, schools, hospitals and factories for precision works, and to be 90 or more in galleries, museums and places for clinical inspection that are required to satisfy a high-level color rendering property. When the general color rendering index Ra of the light emitting device is 80 or more, for example, the device is usable as lightings having a color rendering property for comfortable use in human life environments such as houses, hotels, restaurants and shops. The general color rendering index Ra of the light emitting device may be a higher value so far as the device can have a sterilization effect, and the general color rendering index Ra may be 81 or more, or 85 or more, or 90 or more. When the general color rendering index Ra is 90 or more, the device is usable for color inspection that requires severer visibility, and in galleries, museums and places for clinical inspection.

Preferably, the light emitting device has a specialty color rendering index R12 of 50 or more. The specialty color rendering index R12 indicates a blue color. When the specialty color rendering index R12 of the light emitting device is 50 or more, the device can provide mixed light well balanced between the color components among the light at the intended correlated color temperature from the light emitting device, while preventing blue to blue-green color components in a range of more than 420 nm to 500 nm from decreasing, even when a light emitting element having an emission peak wavelength in a range of 380 nm to 420 nm and capable of emitting a blue-violet color light in a visible range is used as an excitation light source. The specialty color rendering index R12 of the light emitting device is, from the viewpoint of bettering the visibility of substances irradiated with the light emitting device, more preferably 55 or more, even more preferably 60 or more.

The other specialty color rendering indices R9, R10 R11, R13, R14 and R15 than the specialty color rendering index R12 for the blue color of the light emitting device are not specifically limited since the desired visibility and the discriminability of the device vary depending on the site where the device is used. The specialty color rendering index R9 for the red color of the light emitting device may be a minus value, or the specialty color rendering index R9 may be 10 or more. For example, in the case where the light emitting device is used in operation rooms where red color is much observed for the purpose of enhancing the sterilization effect, the numerical value of the specialty color rendering index R9 is preferably higher. In the case where the light emitting deice is used in a place where red color check is unnecessary, the numerical value of the specialty color rendering index R9 of the light emitting device is not specifically limited.

Preferably, the light emitting device is such that the total of the ratio a, the ratio b and the ratio c defined by the expression (1) and by the following expressions (2) and (3) is 2.5 or more and 4.5 or less.

$$\text{Ratio } b = \frac{Y_L/B_L}{Y_S/B_S} \quad (2)$$

In the expression (2), $B_S$ represents a maximum emission intensity in a wavelength range of 430 nm to less than 485 nm in a spectral distribution of a reference light source at the correlated color temperature of the light emitting device, $Y_S$ represents a maximum emission intensity in a wavelength range of 580 nm to less than 610 nm in the spectral distribution of a reference light source at the correlated color temperature of the light emitting device, and the denominator of the expression (2) is a ratio of $Y_S$ to $B_S$, $Y_S/B_S$. In the expression (2), $B_L$ represents a maximum emission intensity in a wavelength range of 430 nm to less than 485 nm in a spectral distribution of the light emitting device, $Y_L$ represents a maximum emission intensity in a wavelength range of 580 nm to less than 610 nm in the spectral distribution of the light emitting device, and the numerator of the expression (2) is a ratio of $Y_L$ to $B_L$, $Y_L/B_L$.

$$\text{Ratio } c = \frac{R_L/B_L}{R_S/B_S} \quad (3)$$

In the expression (3), $B_S$ represents a maximum emission intensity in a wavelength range of 430 nm to less than 485 nm in a spectral distribution of a reference light source at the correlated color temperature of the light emitting device, $R_S$ represents a maximum emission intensity in a wavelength range of 610 nm to 780 nm in the spectral distribution of a reference light source at the correlated color temperature of the light emitting device, and the denominator of the expression (3) is a ratio of $R_S$ to $B_S$, $R_S/B_S$. In the expression (3), $B_L$ represents a maximum emission intensity in a wavelength range of 430 nm to less than 485 nm in a spectral distribution of the light emitting device, $R_L$ represents a maximum emission intensity in a wavelength range of 610 nm to 780 nm in the spectral distribution of the light emitting device, and the numerator of the expression (3) is a ratio of $R_L$ to $B_L$, $R_L/B_L$.

The ratio b defined by the expression (2) is a ratio of the ratio $Y_L/B_L$ as a numerator where $Y_L$ is a maximum emission intensity of a yellow light in a wavelength range of 580 nm to less than 610 nm in the spectral distribution of the light emitting device and $B_L$ is a maximum emission intensity of a blue light in a wavelength range of 430 nm to less than 485 nm, to the ratio $Y_S/B_S$ as a denominator where $Y_S$ is a maximum emission intensity of a yellow light in a wavelength range of 580 nm to less than 610 nm in the spectral distribution of a reference light source at the correlated color temperature of the light emitting device and $B_S$ is a maximum emission intensity of a blue light in a wavelength range of 430 nm to less than 485 nm. The ratio c defined by the expression (3) is a ratio of the ratio $R_L/B_L$ as a numerator where $R_L$ is a maximum emission intensity of a red light in a wavelength range of 610 nm to 780 nm in the spectral distribution of the light emitting device and $B_L$ is a maximum emission intensity of a blue light in a wavelength range of 430 nm to less than 485 nm, to the ratio $R_S/B_S$ as a denominator where $R_S$ is a maximum emission intensity of a red light in a wavelength range of 610 nm to 780 nm in the spectral distribution of a reference light source at the correlated color temperature of the light emitting device and $B_S$ is a maximum emission intensity of a blue light in a wavelength range of 430 nm to less than 485 nm.

Preferably, in the light emitting device, the total of the ratio a defined by the expression (1), the ratio b defined by the expression (2) and the ratio c defined by the expression (3) falls within a range of 2.5 to 4.5, more preferably within a range of 2.6 to 4.5, even more preferably within a range of 2.8 to 4.4. The light emitting device where the total of the ratio a, the ratio b and the ratio c falls within a range of 2.5 to 4.5 is well balanced in point of the color components of the green light, the yellow light and the red light to the blue light from the light emitting device, relative to the color components of the green light, the yellow light and the red right to the blue light from the reference light source at the correlated color temperature of the light emitting device, and has a sterilization effect and a high-level color rendering property.

The range of the ratio b and the range of the ratio c are not specifically limited. Preferably, the total of the ratio a, the ratio b and the ratio c satisfies a range of 2.5 to 4.5. Satisfying the range, also preferably, the ratio b is within a range of 0.8 to 1.7 and the ratio c falls within a range of 0.7 to 1.5.

Preferably, an absolute value B of a value calculated by subtracting the total of the ratio a defined by the expression (1), the ratio b defined by the expression (2) and the ratio c defined by the expression (3) from 3 is 1.5 or less. Here, the absolute value B of the value calculated by subtracting the total of the ratio a, the ratio b and the ratio c from 3 is an absolute value B of a value calculated by subtracting the total of the ratio a, the ratio b and the ratio c from 3, for which the total value in the case where in the ratio a, the ratio b and the ratio c, the ratio $G_L/B_L$, the ratio $Y_L/B_L$ and the ratio $R_L/B_L$ in the spectral distribution of the mixed light from the light emitting device in each wavelength range each are the same as the ratio $G_S/B_S$, the ratio $Y_S/B_S$ and the ratio $R_S/B_S$, respectively, in the spectral distribution of a reference light source at the correlated color temperature of the light emitting device, is referred to as 3. Regarding the absolute value B of a value calculated by subtracting the total of the ratio a, the ratio b and the ratio c from 3, when the correlated color temperature of the light emitting device is nearer to that of the reference light source, the light emitting device can emit mixed light well balanced in the blue color component, the green color component, the yellow color component and the red color component. When the absolute value B of a value calculated by subtracting the total of the ratio a, the ratio b and the ratio c from 3 is 1.5 or less, the light emitting device can emit mixed light nearer to the mixed light from a reference light source at the correlated color temperature of the light emitting device and well balanced in the blue color component, the green color component, the yellow color component and the red color component, even though the light emitting device can emit a light of a blue color component having a germicidal effect. The absolute value B of a value calculated by subtracting the total of the ratio a, the ratio b and the ratio c from 3 may be 1.4 or less, or may be 1.3 or less.

In the light emitting device, the fluorescent material contained in the fluorescent member preferably contains at least one fluorescent material selected from the group consisting of a first fluorescent material having an emission peak wavelength in a range of 430 nm to less than 485 nm, as excited by the light from the light emitting element having an emission peak wavelength in a range of 380 nm to 420 nm, a second fluorescent material having an emission peak wavelength in a range of 485 nm to less than 610 nm, as excited by the light from the light emitting element, and a third fluorescent material having an emission peak wavelength in a range of 610 nm to 780 nm, as excited by the light from the light emitting element.

The first fluorescent material emits, as excited by the light from the light emitting element, a light of a blue-violet color to a blue color having an emission peak wavelength in a range of 430 nm to less than 485 nm. In the mixed light from the light emitting device containing the first fluorescent material, the light of a blue color component that is poor in the light from the light emitting element having an emission peak in a range of 380 nm to 420 nm is compensated by the first fluorescent material. The light emitting device can exhibit a sterilization effect owing to the light from the light emitting element and can emit mixed light having a high-level color rendering property.

Preferably, the first fluorescent material contains at least one fluorescent material selected from the group consisting of a fluorescent material containing a halogen-containing alkaline earth metal phosphate containing at least one alkaline earth metal element, and at least one halogen element, and Eu as an activator, and a fluorescent material containing an alkaline earth metal silicate containing at least one element selected from the group consisting of Ba, Sr and Ca, and Mg in the composition and Eu as an activating element. The first fluorescent material may contain two or more kinds of fluorescent materials. More preferably, the first fluorescent material contains a halogen-containing alkaline earth metal phosphate containing at least one alkaline earth metal element, and at least one halogen element, and Eu as an activator.

Preferably, the first fluorescent material contains at least one fluorescent material selected from the group consisting of a fluorescent material having a composition represented by the following formula (I) and a fluorescent material having a composition represented by the following formula (II), and may contain two or more kinds of fluorescent materials. More preferably, the first fluorescent material contains a fluorescent material having a composition represented by the following formula (I).

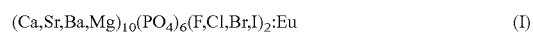

$(Ca,Sr,Ba,Mg)_{10}(PO_4)_6(F,Cl,Br,I)_2:Eu$ (I)

$(Ba,Sr,Ca)_3MgSi_2O_8:Eu$ (II)

In this description, in the formulae representing the compositions of the fluorescent materials, plural elements sectioned by the comma (,) mean that at least one element of these plural elements is contained in the composition. The plural elements sectioned by the comma (,) in the compositional formulae mean that at least one element selected from the plural elements thus sectioned by the comma is contained in the composition and two or more kinds of the plural elements may be contained in combination. In this description, in the formulae representing the compositions of the fluorescent materials, the part before the colon (:) represents the elements and the molar ratio constituting a host crystal and the part after the colon (:) represents an activating element.

The second fluorescent material emits a light of a blue-green color to an orange color having an emission peak wavelength in a range of 485 nm to less than 610 nm, as excited by the light from the light emitting element. In the mixed light from the light emitting device containing the second fluorescent material, the light of a color component insufficient in the light from the light emitting element and the light from the first fluorescent material is compensated by the second fluorescent material. The light emitting device has a sterilization effect owing to the light emitted from the light emitting element, and emits mixed light having a high-level color rendering property.

Preferably, the second fluorescent material contains at least one fluorescent material selected from the group consisting of a fluorescent material containing a rare earth aluminate containing at least one rare earth element except Ce, and Al, and optionally Ga in the composition and Ce as an activating element, a fluorescent material containing a halogen-containing alkaline earth metal silicate containing at least one alkaline earth metal element selected from the group consisting of Ca, Sr and Ba, and at least one halogen element selected from the group consisting of F, Cl and Br in the composition, and Eu as an activating element, a fluorescent material containing a β-SiAlON with Eu as an activating element, as well as a fluorescent material containing a rare earth nitride containing at least one rare earth element selected from the group consisting of La, Y and Gd, and Si in the composition and Ce as an activating element, and a fluorescent material containing an alkaline earth metal silicate with Eu as an activating element, and may contain two or more second fluorescent materials.

Preferably, the second fluorescent material contains at least one fluorescent material selected from the group consisting of a fluorescent material having a composition represented by the following formula (III), a fluorescent material having a composition represented by the following formula (IV), a fluorescent material having a composition represented by the following formula (V), a fluorescent material having a composition represented by the following formula (VI), and a fluorescent material having a composition represented by the following formula (VII), and may contain two or more fluorescent materials.

$(Lu,Y,Gd,Tb)_3(Al,Ga)_5O_{12}:Ce$ (III)

$(Ca,Sr,Ba)_8MgSi_4O_{16}(F,Cl,Br)_2:Eu$ (IV)

$Si_{6-z}Al_zO_zN_{8-z}:Eu(0<z<4.2)$ (V)

$(La,Y,Gd)_3Si_6N_{11}:Ce$ (VI)

$(Ba,Sr,Ca,Mg)_2SiO_4:Eu$ (VII)

The third fluorescent material emits a light of a red color having an emission peak wavelength in a range of 610 nm to 780 nm, as excited by the light from the light emitting element. In the mixed light from the light emitting device containing the third fluorescent material, the light of a color component insufficient in the light from the light emitting element and the light from the first fluorescent material and the second fluorescent material is compensated by the third fluorescent material. The light emitting device has a sterilization effect owing to the light emitted from the light emitting element, and emits mixed light having a high-level color rendering property.

Preferably, the third fluorescent material contains at least one fluorescent material selected from the group consisting of a fluorescent material containing a nitride containing at least one alkaline earth metal element, and Al, and Si in the composition and Eu as an activating element, a fluorescent material containing a nitride containing at least one alkaline earth metal element, and Si in the composition and Eu as an activating element, and a fluorescent material containing a nitride containing at least one alkaline earth metal, and Li and Al in the composition and Eu as an activating element, and may contain two or more kinds of third fluorescent materials. More preferably, the third fluorescent material contains a fluorescent material containing a nitride containing at least one alkaline earth metal element, and Al, and Si in the composition and Eu as an activating element.

Preferably, the third fluorescent material contains at least one fluorescent material selected from the group consisting of a fluorescent material having a composition represented by the following formula (VIII), a fluorescent material having a composition represented by the following formula (IX), and a fluorescent material having a composition represented by the following formula (X), and may contain two or more kinds of fluorescent materials. More preferably, the third fluorescent material contains a fluorescent material having a composition represented by the following formula (VIII).

$(Sr,Ca)AlSiN_3:Eu$ (VIII)

$(Ca,Sr,Ba)_2Si_5N_8:Eu$ (IX)

$(Sr,Ca)LiAl_3N_4:Eu$ (X)

Relative to the total mass of the fluorescent material, preferably, the content of the first fluorescent material is within a range of 1.0% by mass to 50.0% by mass, the content of the second fluorescent material is within a range of 45.0% by mass to 99.0% by mass, and the content of the third fluorescent material is within a range of 0% by mass to 50.0% by mass. In the total mass of the fluorescent material, when the content of each fluorescent material of the first fluorescent material, the second fluorescent material and the third fluorescent material falls within the above-mentioned range, the light emitting device can have a sterilization effect owing to the light from the light emitting element having an emission peak wavelength in a range of 380 nm to 420 nm and can have an enhanced color rendering property. The third fluorescent material may not be in the fluorescent material so far as the light emitting device can satisfy an intended color rendering property at a targeted correlate color temperature. In the total mass of the fluorescent material, more preferably, the content of the first fluorescent material is within a range of 1.0% by mass to 49.0% by mass, the content of the second fluorescent material is within a range of 45.0% by mass to 98.0% by mass, and the content of the third fluorescent material is within a range of 1.0% by mass to 49.0% by mass. Even more preferably, in the total mass of the fluorescent material, the content of the first fluorescent material is within a range of 2.0% by mass to 48.0% by mass, the content of the second fluorescent material is within a range of 45.0% by mass to 96.0% by mass, and the content of the third fluorescent material is within a range of 2.0% by mass to 48.0% by mass.

Figure 2:
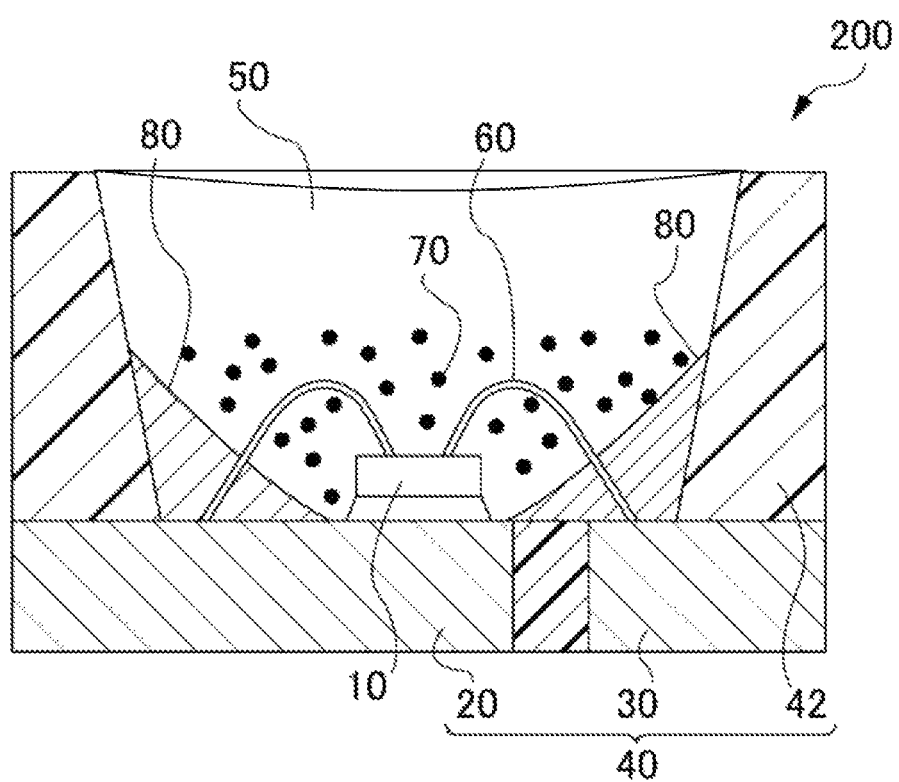
FIG. 2 is a schematic cross-sectional view showing a second example of a light emitting device.

FIG. 2 is a schematic cross-sectional view showing a second example of a light emitting device. As shown in FIG. 2, a light emitting device 200 is provided with a molded body 40 where a light emitting element 10 and a fluorescent material 50 are arranged, and in the side wall direction of the light emitting element 10 arranged in the molded body 40, a reflective member 80 containing an oxide having a reflectance at 405 nm of 50% or more and a resin is arranged from the bottom to the inner side wall of the concave portion of the molded body 40. Since the reflective member 80 is arranged in the side wall direction of the light emitting element 10 arranged in the molded body 40, the light from the light emitting element 10 having an emission peak wavelength in a rage of 380 nm or more and 420 nm or less can be efficiently reflected by the reflective member 80 and a light having an emission peak wavelength in a range of 380 nm to 420 nm having a high germicidal effect can be efficiently emitted from the light emitting device to enhance the sterilization effect of the device.

Preferably, the oxide having a reflectance at 405 nm of 50% or more contained in the reflective member 80 is an oxide containing at least one selected from the group consisting of yttrium, zirconium, aluminum and titanium. When such an oxide is contained in the reflective member 80, the light from the light emitting element can be efficiently emitted from the light emitting device to enhance the sterilization effect of the device.

The resin contained in the reflective member 80 includes a thermoplastic resin and a thermosetting resin. The resin contained in the reflective member 80 may be the same resin as that contained in the resin part 42 to constitute the molded body 40, or may be a resin different from the resin contained in the resin part 42.

Figure 3:
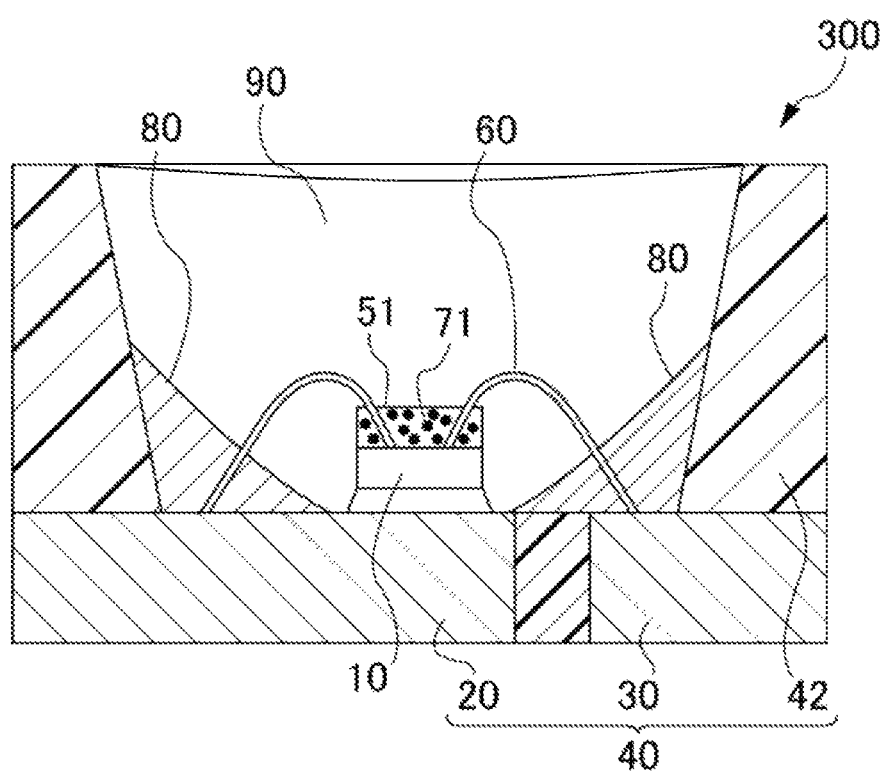
FIG. 3 is a schematic cross-sectional view showing a third example of a light emitting device.

FIG. 3 is a schematic cross-sectional view showing a third example of a light emitting device. As shown in FIG. 3, in the light emitting device 300, a fluorescent member 51 is arranged on the top of the light emitting element 10, and the side surface of the light emitting element 10 is exposed out of the fluorescent member 51 and the reflective member 80. When the fluorescent member 51 is arranged on the top of the light emitting element 10 and the side surface of the light emitting element 10 is exposed out of the fluorescent member 51 and the reflective member 80, light having an emission peak wavelength within a range of 380 nm to 420 nm and having a germicidal effect is emitted from the side surface of the light emitting element 10 without being subjected to wavelength conversion through the fluorescent material 71, directly from the light emitting element 10 toward the outside of the light emitting device 300 and the sterilization effect of the device can be enhanced. A part of the light from the light emitting element 10 is subjected to wavelength conversion through the fluorescent material 71 contained in the fluorescent member 51 arranged on the top of the light emitting element 10, and the light from the light emitting element 10 and the light having been subjected to wavelength conversion through the fluorescent material 71 contained in the fluorescent member 51 are emitted from the light emitting device 300 to give mixed light having a desired color rendering property. The light emitting element 10 may be exposed out of the fluorescent member 51 and the reflective member 80, and inside the concave portion having a bottom surface and a side surface of the molded body 40, a sealing member 90 of a sealing material may be arranged in the part except the part where the light emitting element 10, the fluorescent member 51, the reflective member 80 and the wire 60 are arranged. The sealing member 90 does not contain a fluorescent material 70. Examples of the sealing material include a silicone resin and an epoxy resin. The resin contained in the sealing member 90 may be the same as the resin contained in the resin part 42 of the molded body 40, the resin contained in the reflective member 80 and the resin contained in the fluorescent member 51, or may differ from the latter. Like the fluorescent members 50 and 51, the sealing member 90 may contain any other component such as a filler, a light stabilizer and a colorant in addition to the sealing material. Examples of the filler include silica, barium titanate, titanium oxide, and aluminum oxide.

The fluorescent member 51 to be arranged on the top of the light emitting element 10 is so arranged on the top of the light emitting element 10 that light not subjected to wavelength conversion through a fluorescent material can be emitted from the light emitting device, and may be so arranged as not to be on any other than the top of the light emitting element 10.

Figure 4:
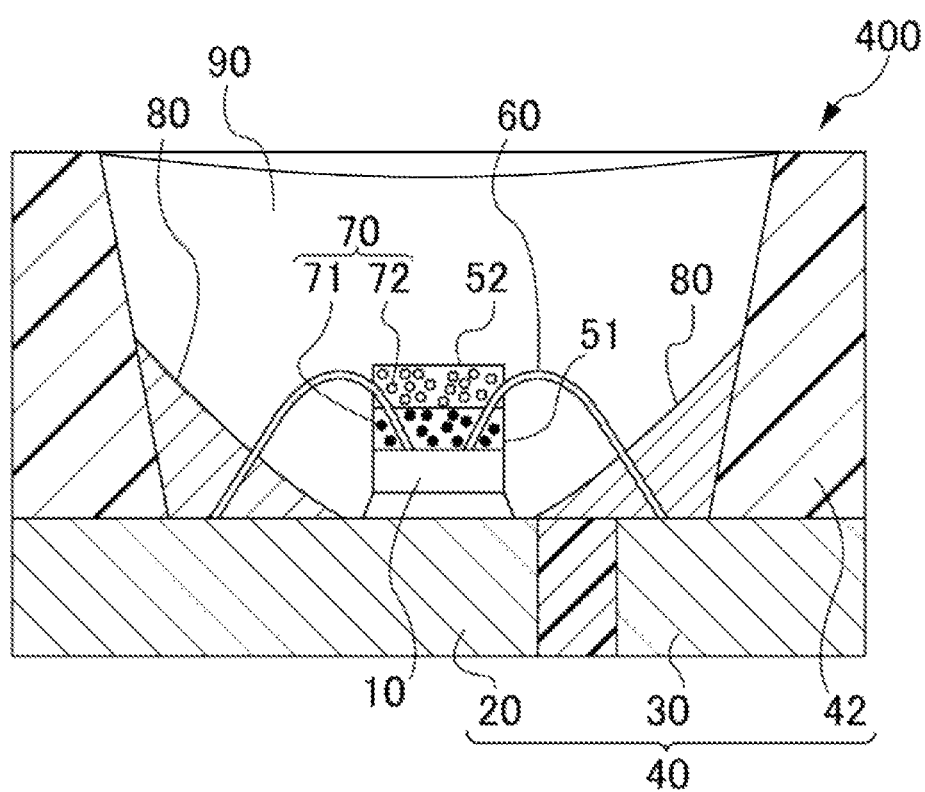
FIG. 4 is a schematic cross-sectional view showing a fourth example of a light emitting device.

FIG. 4 is a schematic cross-sectional view showing a fourth example of a light emitting device. As shown in FIG. 4, the light emitting device 400 is provided with a first fluorescent member 51 containing a fluorescent material 71 having a reflectance at 405 nm of 1% or more and 50% or less, and a second fluorescent member 52 containing a fluorescent material 72 having a higher reflectance at 405 nm than that of the fluorescent material 71 contained in the first fluorescent member 51. The first fluorescent member 51 is arranged on the top of the light emitting element 10, and the second fluorescent member 52 is arranged on the first fluorescent member 51. In the light emitting device 400 shown in FIG. 4, a part of the light from the light emitting element 10 is subjected to efficient wavelength conversion through the fluorescent material contained in the first fluorescent member 51 and having a reflectance at 405 nm of 1% or more and 50% or less, and further the light from the light emitting element 10 and the light having been subjected to wavelength conversion through the fluorescent material 71 form mixed light having intended emission efficiency and color rendering property and comfortably usable in human visual environments. The fluorescent material 72 contained in the second fluorescent member 52 has a higher reflectance at 405 nm than that of the fluorescent material 71 contained in the first fluorescent member 51, and the light from the first fluorescent member 51 can be subjected to wavelength conversion more efficiently than the light from the light emitting element 10 to give light having intended emission efficiency and color rendering property. The fluorescent material 72 contained in the second fluorescent member 52 may be a fluorescent material having a higher reflectance at 405 nm than the fluorescent material 71 having a reflectance at 405 nm of 1% or more and 50% or less contained in the first fluorescent member 51. For example, in the case where the fluorescent material 71 contained in the first fluorescent member 51 is a fluorescent material 71 having a reflectance at 405 nm of 1%, the fluorescent material 72 contained in the second fluorescent member 52 may be a fluorescent material 72 having a reflectance at 405 nm of more than 1%, or may be a fluorescent material having a reflectance at 405 nm of 50% or less. For example, in the case where the fluorescent material 71 contained in the first fluorescent member 51 is a fluorescent material 71 having a reflectance at 405 nm of 50%, the fluorescent material 72 contained in the second fluorescent member 52 may be a fluorescent material 72 having a reflectance at 405 nm of more than 50%.

The fluorescent material 71 contained in the first fluorescent member 51 may be a fluorescent material having a reflectance at 405 nm of 1% or more and 50% or less. The fluorescent material 71 contained in the first fluorescent member 51 preferably contains at least one fluorescent material selected from the group consisting of the first fluorescent material, the second fluorescent material and the third fluorescent material, and may contain two or more kinds of fluorescent materials. The fluorescent material 72 contained in the second fluorescent member 52 may be a fluorescent material whose reflectance at 405 nm is higher than that of the fluorescent material 71 contained in the first fluorescent material 51. The fluorescent material 72 contained in the second fluorescent member 52 preferably contains at least one fluorescent material selected from the group consisting of the first fluorescent material, the second fluorescent material and the third fluorescent material, and may contain two or more kinds of fluorescent materials.

The first fluorescent member 51 is so arranged on the top of the main surface of the light emitting element 10 that the light from the light emitting element 10 could be subjected to wavelength conversion through the fluorescent material 71 contained in the first fluorescent member 51 and could be emitted from the light emitting device 400. As shown in FIG. 4, the second fluorescent member 52 is arranged on the first fluorescent member 51. The side surface of the light emitting element 10 may be exposed out of the first fluorescent member 51, the second fluorescent member 52 and the reflective member 80 so that the light from the light emitting element 10 could be emitted out from the light emitting device 400 without being subjected to wavelength conversion through the fluorescent material 71 contained in the first fluorescent member 51 and through the fluorescent material 72 contained in the second fluorescent member 52.

Figure 5:
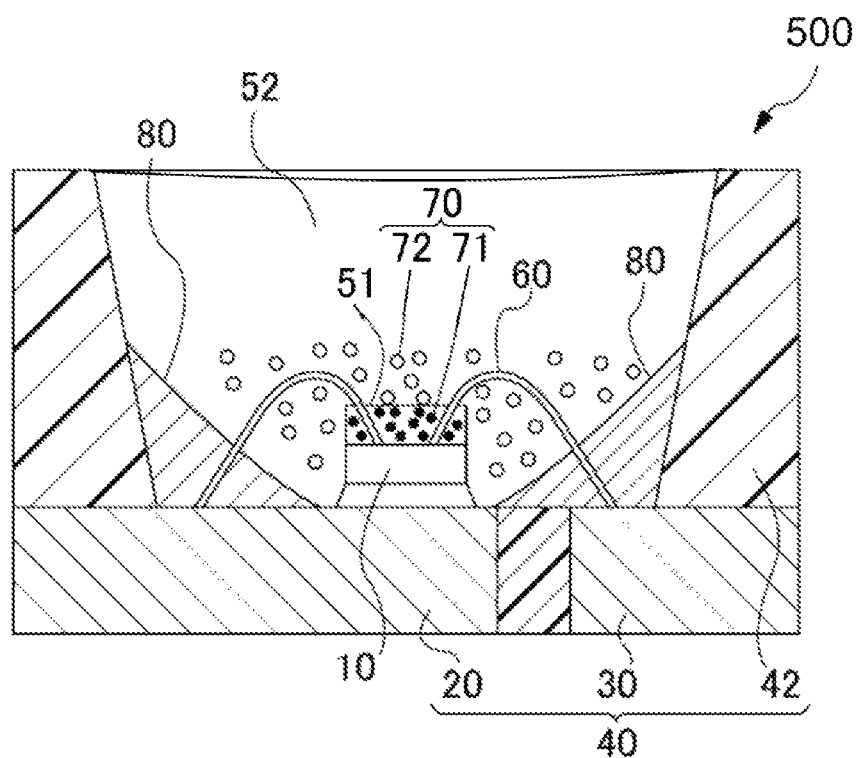
FIG. 5 is a schematic cross-sectional view showing a fifth example of a light emitting device.

FIG. 5 is a schematic cross-sectional view showing a fifth example of a light emitting device. As in the light emitting device 500 shown in FIG. 5, the second fluorescent member 52 may be arranged on the first fluorescent member 51 and the reflective member 80 to cover the side surface of the light emitting element 10 so that the side surface of the light emitting element 10 could not be exposed out of the second fluorescent member 52.

Figure 6:
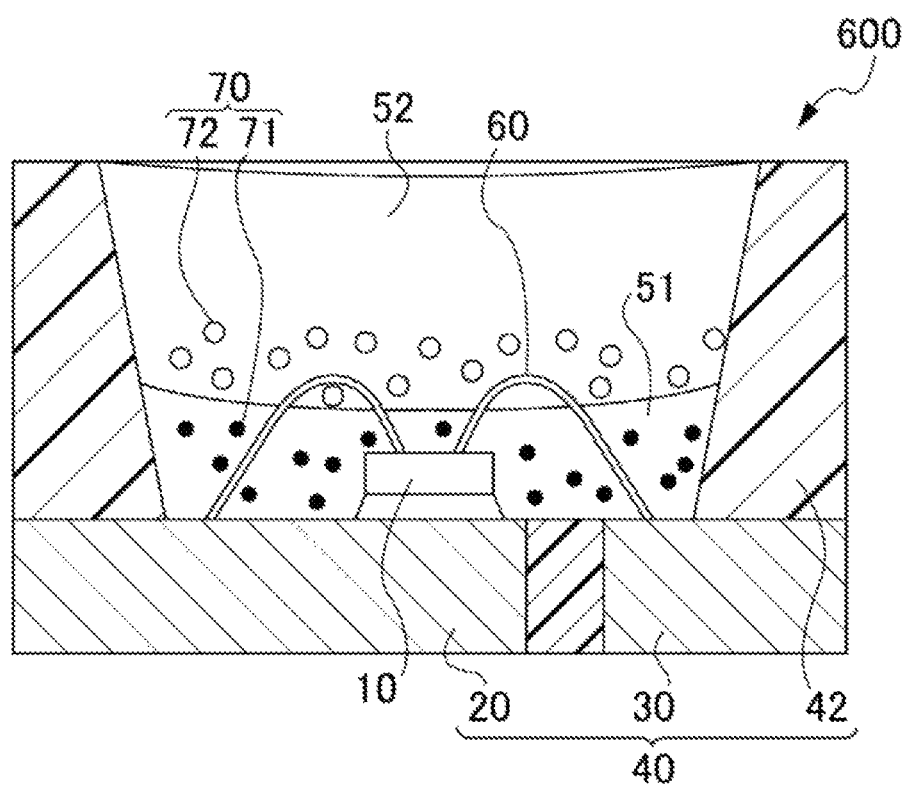
FIG. 6 is a schematic cross-sectional view showing a sixth example of a light emitting device.

FIG. 6 is a schematic cross-sectional view showing a sixth example of a light emitting device. In the light emitting device 600 shown in FIG. 6, the first fluorescent member 51 is so arranged as to cover the top and the side surface of the light emitting element 10, and the second fluorescent member 52 may be arranged on the first fluorescent member 51. In the light emitting device 600 shown in FIG. 6, the fluorescent material 71 contained in the first fluorescent member 51 has a reflectance at 405 nm of 1% or more and 50% or less, and through the fluorescent material 71, the light emitted from the light emitting element 10 is efficiently subjected to wavelength conversion. In the light emitting device 600, the light having been subjected to wavelength conversion through the fluorescent material 71 contained in the first fluorescent member 51 is further subjected to efficient wavelength conversion through the fluorescent material 72 having a reflectance at 405 nm higher than that of the fluorescent material 71 and contained in the second fluorescent member 52. The light emitting device 600 emits a mixture of light from the light emitting element 10, light having been subjected to wavelength conversion through the fluorescent material 71, and light having been subjected to wavelength conversion through the fluorescent material 72, and the mixed light has intended emission efficiency and color rendering property comfortably usable in human visual environments. The fluorescent material 72 contained in the second fluorescent member 52 has a reflectance at 405 nm higher than that of the fluorescent material 71 contained in the first fluorescent member 51, and the light having been subjected to wavelength conversion through the fluorescent material 71 contained in the first fluorescent member 51 can be more efficiently subjected to wavelength conversion through the fluorescent material 72 contained in the second fluorescent member 52, than the light emitted from the light emitting element 10.

Figure 7:
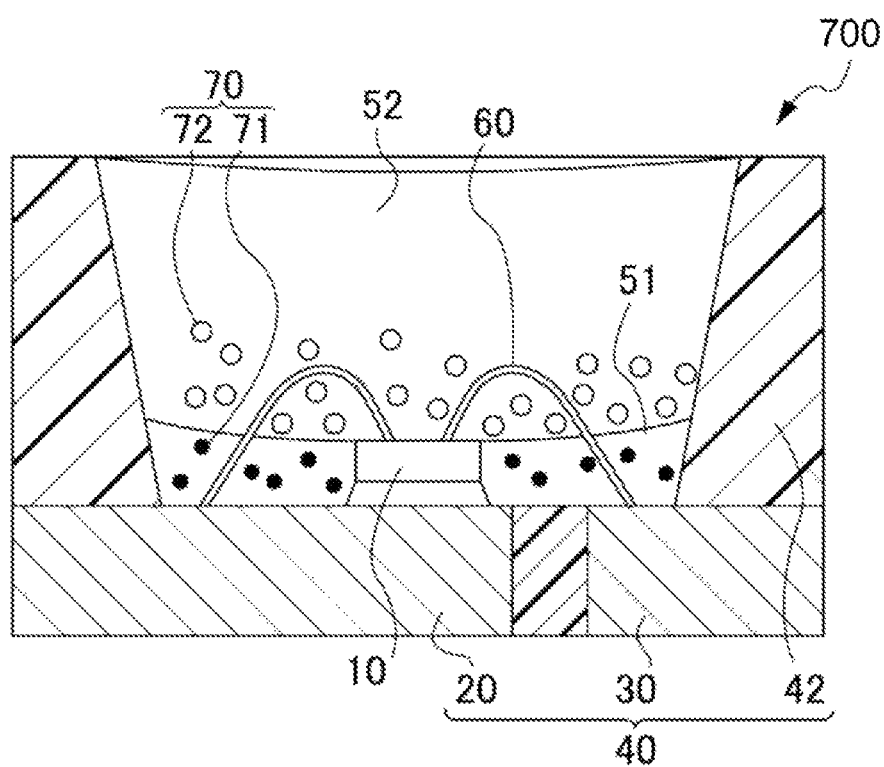
FIG. 7 is a schematic cross-sectional view showing a seventh example of a light emitting device.

FIG. 7 is a schematic cross-sectional view showing a seventh example of a light emitting device. In the light emitting device 700 shown in FIG. 7, the first fluorescent member 51 is arranged around the side surface of the light emitting element 10, and the second fluorescent member 52 is arranged so as to cover the top of the light emitting element 10 and the first fluorescent member 51. The top of the light emitting element 10 in the light emitting device 700 is exposed out of the first fluorescent member 51 and is covered with the second fluorescent member 52. The top of the light emitting element 10 in the light emitting device 700 is exposed out of the first fluorescent member 51, and the light from the light emitting element 10 can be easily taken out of the light emitting device 700 and a light component having a germicidal effect can be readily taken out of the light emitting device 700. When a light component having a germicidal effect is emitted from the light emitting device 700, the sterilization effect of the device can be enhanced and, in addition, through the fluorescent material 71 contained in the first fluorescent member 51 that covers the side surface of the light emitting element 10, and through the fluorescent material 72 contained in the second fluorescent member 52 to cover the top of the light emitting element 10 and the top of the first fluorescent member 51, the light emitted from the light emitting element 10 can be subjected to wavelength conversion, and accordingly, the light emitting device 700 can emit light having intended emission efficiency and color rendering property and comfortably usable in human visual environments.

EXAMPLES

The present invention is hereunder specifically described by reference to the following Examples. The present invention is not limited to these Examples.

Fluorescent Materials

The first fluorescent material, the second fluorescent material and the third fluorescent material used in Examples and Comparative Examples are shown in Table 1.

Average Particle Size of Fluorescent Material

As an average particle size of fluorescent material, a Fisher Sub Sieve Sizer's number of each fluorescent material was measured according to an air permeation method using Fisher Sub Sieve Sizer. Briefly, 1 cm$^3$ of a sample was weighed and packed in a special tubular container, then dry air under a predetermined pressure was applied, a specific surface area of the sample was read from the differential pressure, and the data were averaged to give an average particle size.

Emission Peak Wavelength

As an emission peak wavelength of each fluorescent material, an emission peak wavelength was determined from the emission spectrum measured using each a fluorospectrophotometer (QE-2000, manufactured by Otsuka Electronics Co., Ltd., or F-4500, manufactured by Hitachi High-Technologies Corp.). The first fluorescent material was irradiated with light of excitation wavelength 405 nm to measure the emission spectrum. The second fluorescent material and the third fluorescent material were irradiated with light of excitation wavelength 450 nm to measure each the emission spectrum.

TABLE 1

|  | Name of Fluorescent Material | Peak Wavelength (nm) | Compositional Formula | Average Particle Size (μm) |
|---|---|---|---|---|
| First Fluorescent Material | CCA | 460 | $Ca_5(PO_4)_3Cl:Eu$ | 10.0 |
| Second Fluorescent Material | YAG-1 | 543 | $Y_3(Al, Ga)_5O_{12}:Ce$ | 22.0 |
|  | YAG-2 | 547 | $Y_3Al_5O_{12}:Ce$ | 22.0 |

TABLE 1-continued

|  | Name of Fluorescent Material | Peak Wavelength (nm) | Compositional Formula | Average Particle Size (μm) |
|---|---|---|---|---|
|  | LAG-1 | 545 | $Lu_3Al_5O_{12}$:Ce | 18.5 |
|  | β-SiAlON | 543 | $(Si, Al)_6(O, N)_8$:Eu | 13.0 |
|  | Chlorosilicate | 522 | $Ca_8MgSi_4O_{16}Cl_2$:Eu | 11.0 |
|  | LSN | 544 | $La_3Si_6N_{11}$:Ce | 16.5 |
| Third Fluorescent Material | SCASN-1 | 630 | $(Sr, Ca)AlSiN_3$:Eu | 10.0 |
|  | SCASN-2 | 640 | $(Sr, Ca)AlSiN_3$:Eu | 13.0 |
|  | SCASN-3 | 620 | $(Sr, Ca)AlSiN_3$:Eu | 10.0 |

Example 1

In the light emitting device 200, a light emitting element 10 having an emission peak wavelength of 405 nm was used. A silicone resin was used as the sealing material to constitute the fluorescent member 50. A fluorescent material containing a halogen-containing alkaline earth metal phosphate was used as the first fluorescent material, a fluorescent material containing a rare earth aluminate was used as the second fluorescent material, and a fluorescent material containing a nitride was used as the third fluorescent material. The first fluorescent material, the second fluorescent material and the third fluorescent material used in Examples and Comparative Examples are shown in Table 1. The first fluorescent material, the second fluorescent material and the third fluorescent material were so blended that the correlated color temperature of the mixed light of the light from the light emitting element 10 and the light from the fluorescent material 70 containing the first fluorescent material, the second fluorescent material and the third fluorescent material could be around 3500 K. The content of each fluorescent material relative to the total mass 100% of the first fluorescent material, the second fluorescent material and the third fluorescent material is shown in Table 2. The fluorescent material 70 containing the first fluorescent material, the second fluorescent material and the third fluorescent material was added to a silicone resin, mixed and dispersed, and then defoamed to produce a fluorescent member composition for constituting a fluorescent member. On the other hand, titanium oxide having a reflectance at 405 nm of 56.5% was added to a silicone resin, mixed and dispersed, and then defoamed to produce a reflective member composition. Into the concave portion of the molded body 40, the reflective member composition was cast, and the reflective member composition was so arranged and cured that the side surface direction of the light emitting element 10 could be exposed out of the reflective member composition, forming the reflective member 80. The resultant fluorescent member composition was cast onto the reflective member 80 and the light emitting element 10 in the concave portion of the molded body 40 and filled into the concave portion of the molded body 40, and further heated at 150° C. for 3 hours to cure the fluorescent member composition to form the fluorescent member 50, and accordingly the light emitting device 200 as shown in FIG. 2 was produced. The reflectance at a wavelength 405 nm of titanium oxide was measured using a fluorospectrophotometer (F-4500, manufactured by Hitachi High-Technologies Corp.). Specifically, the reflectance of titanium oxide w was measured using a calcium hydrogen phosphate ($CaHPO_4$) as a reference sample.

Examples 2 to 10

Light emitting devices of Examples 2 to 10 were produced in the same manner as in Example 1, except that the kind of the first fluorescent material, the second fluorescent material and the third fluorescent material and the content of each fluorescent material relative to the total mass of the fluorescent materials were changed as in Table 2 and the first fluorescent material, the second fluorescent material and the third fluorescent materials were blended.

Comparative Example 1

A light emitting device of Comparative Example 1 was produced in the same manner as in Example 1, except that a light emitting element having an emission peak wavelength of 450 nm was used, the first fluorescent material was not used, the kind of the second fluorescent material and the third fluorescent material and the content of each fluorescent material relative to the total mass of the fluorescent materials were changed as in Table 2 and the second fluorescent material and the third fluorescent material were blended.

Comparative Examples 2 and 3

Light emitting devices of Comparative Examples 2 and 3 were produced in the same manner as in Example 1, except that the first fluorescent material was not used, the kind of the second fluorescent material and the third fluorescent material and the content of each fluorescent material relative to the total mass of the fluorescent materials were changed as in Table 2 and the second fluorescent material and the third fluorescent material were blended.

The light emitting devices of Examples and Comparative Examples were evaluated as follows.

Emission Spectrum (Spectral Distribution)

Figure 21:
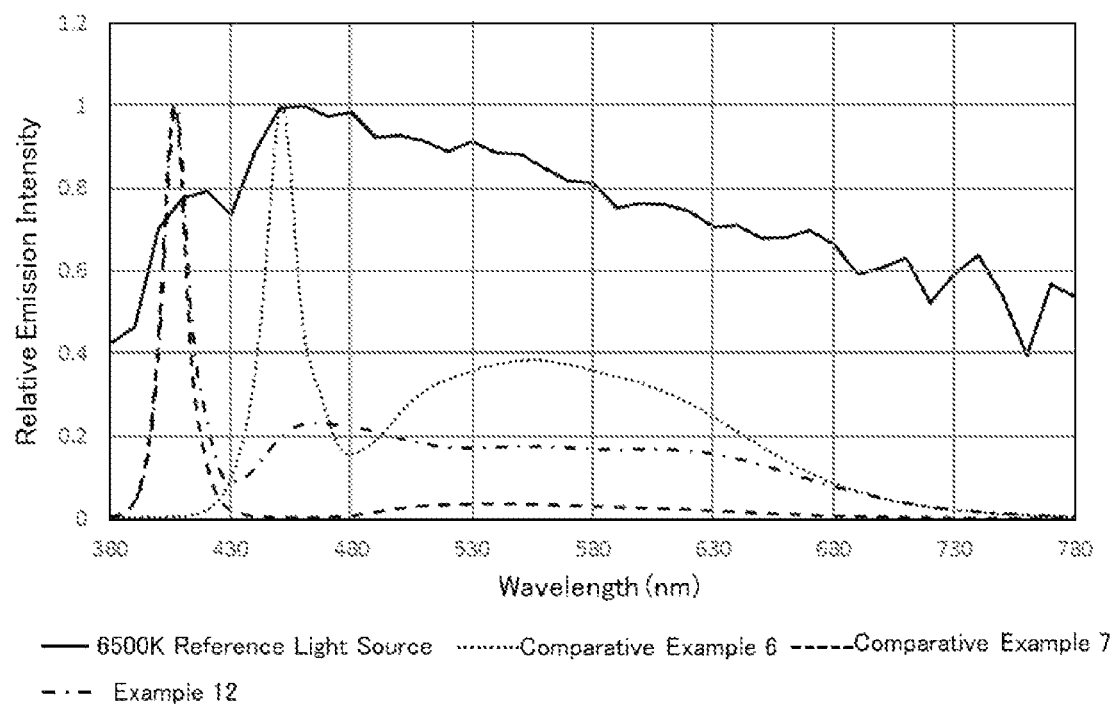
FIG. 21 is a graph showing an emission spectrum of the light emitting device of Example 12 and Comparative Examples 6 and 7 at a correlated color temperature around 6500 K, and an emission spectrum of a reference light source (CIE daylight) at a correlated color temperature 6500 K.

Using an optical measurement system including a combination of a multichannel spectroscope and an integrating sphere, the emission spectrum (spectral distribution) of the mixed light from the light emitting device of Examples and Comparative Examples was measured. The results are shown in FIGS. 14, 15, 18, 21 and 24. In FIGS. 14, 15, 18 and 24, a spectrum of a complete radiator at the correlated color temperature of each light emitting device in a range of 2000 K to 5000 K is shown as a spectrum of a reference light source. In FIG. 21, a spectrum of a CIE daylight at the correlated color temperature in Example 12 in a range of more than 5000 K is shown as a spectrum of a reference light source.

380 nm to 420 nm Emission Amount/Total Emission Amount

In the spectral distribution of the light emitting device of Examples and Comparative Examples, a proportion of the integral value over a wavelength range of 380 nm to 420 nm (380 nm to 420 nm emission amount) relative to the integral value over a wavelength range of 380 nm to 780 nm (total emission amount) normalized to 100% was calculated. The results are shown in Table 2 to Table 5.

Ratio a, Ratio b, Ratio c, and Total of These

Figure 10:
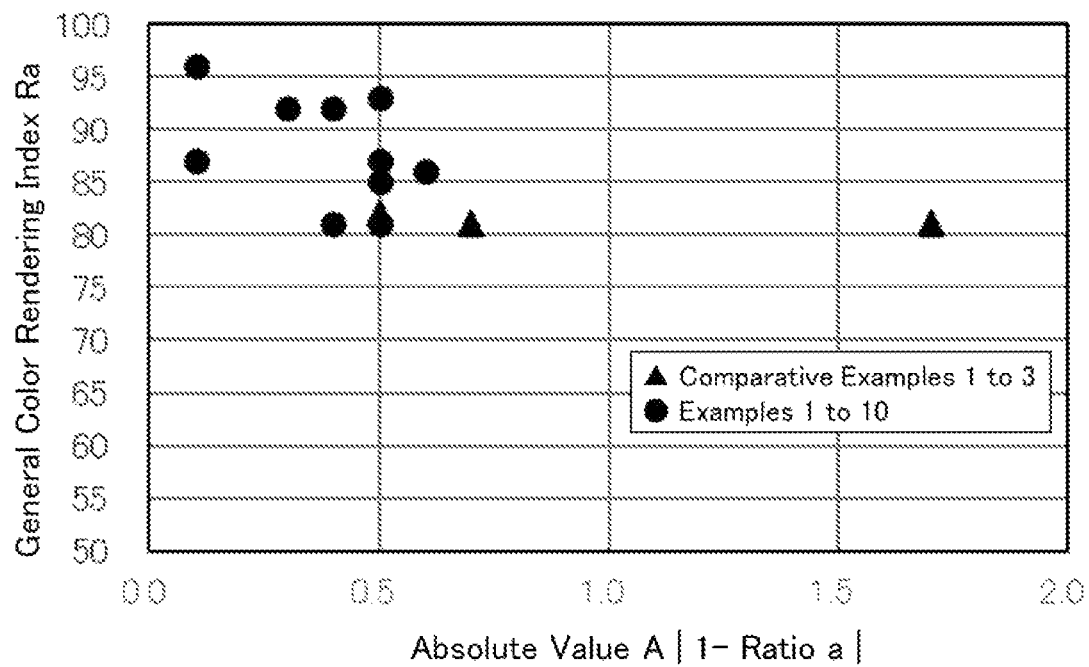
FIG. 10 is a graph plotted between the absolute value A of a value calculated by subtracting, from 1, the ratio a obtained from the emission spectrum of mixed light emitted from each of the light emitting devices of Examples 1 to 10 and Comparative Examples 1 to 3 and the general color rendering index Ra of each device.
Figure 11:
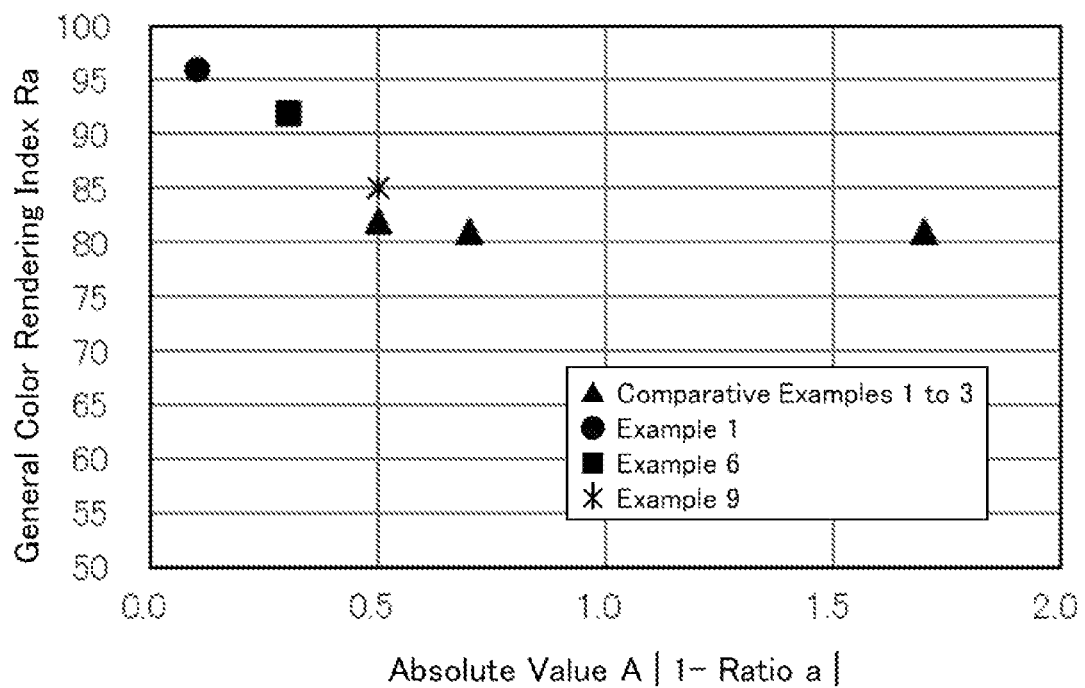
FIG. 11 is a graph plotted between the absolute value A of a value calculated by subtracting, from 1, the ratio a obtained from the emission spectrum of mixed light emitted from each of the light emitting devices of Examples 1, 6 and 9 and Comparative Examples 1 to 3 and the general color rendering index Ra of each device.

From the emission spectrum (spectral distribution) of the light emitting device of Examples and Comparative Examples, the ratio a, the ratio b and the ratio c defined by the expression (1), the expression (2) and the expression (3), respectively, and the total (ratios a+b+c) were calculated. In addition, an absolute value A of a value calculated by subtracting the ratio a from 1, and an absolute value B of a value calculated by subtracting the total of the ratio a, the ratio b and the ratio c from 3 were determined. The results are shown in Table 2 to Table 9. In FIGS. 8, 16, 19 and 22, the abscissa indicates the ratio a, the ordinate indicates the general color rendering index Ra, and the ratio a and the general color rendering index Ra obtained from the emission spectrum of the mixed light from the light emitting device of Examples and Comparative Examples are plotted. In FIGS. 9, 17, 20 and 23, the abscissa indicates a total of the ratio a, the ratio b and the ratio c, the ordinate indicates the general color rendering index Ra, and the total of the ratio a, the ratio b and the ratio c, and the general color rendering index Ra obtained from the emission spectrum of the mixed light from the light emitting device of Examples and Comparative Examples are plotted. In FIGS. 10 and 11, the abscissa indicates the absolute value A of a value calculated by subtracting the ratio a from 1, the ordinate indicates the general color rendering index Ra, and the absolute value A and the general color rendering index Ra obtained from the emission spectrum of the mixed light from the light emitting device of Examples and Comparative Examples are plotted.

Figure 12:
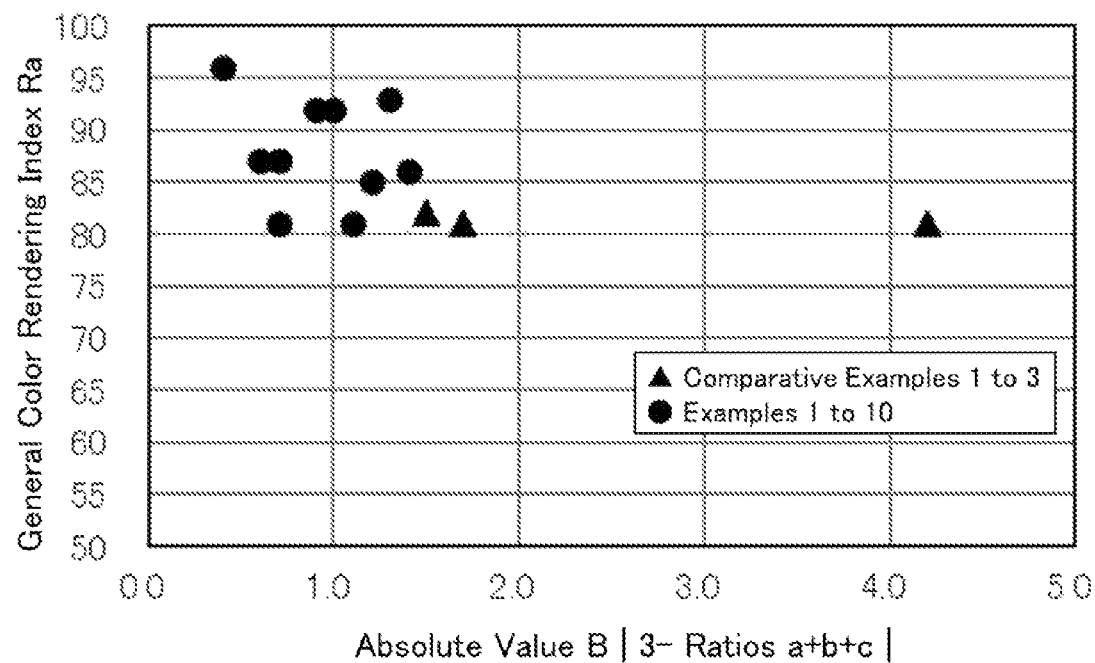
FIG. 12 is a graph plotted between the absolute value B of a value calculated by subtracting, from 3, the total of the ratios a, b and c obtained from the emission spectrum of mixed light emitted from each of the light emitting devices of Examples 1 to 10 and Comparative Examples 1 to 3 and the general color rendering index Ra of each device.
Figure 13:
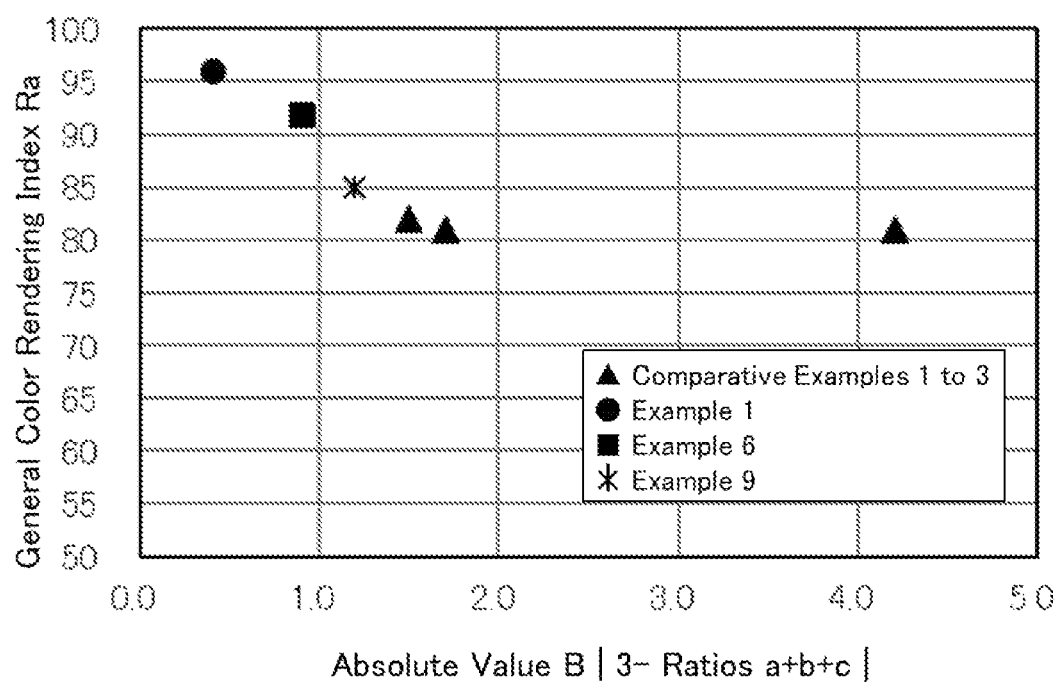
FIG. 13 is a graph plotted between the absolute value B of a value calculated by subtracting, from 3, the total of the ratios a, b and c obtained from the emission spectrum of mixed light emitted from each of the light emitting devices of Examples 1, 6 and 9 and Comparative Examples 1 to 3 and the general color rendering index Ra of each device.

In FIGS. 12 and 13, the abscissa indicates the absolute value B of a value calculated by subtracting, from 3, the total of the ratio a, the ratio b and the ratio c, the ordinate indicates the general color rendering index Ra, and the absolute value B and the general color rendering index Ra obtained from the emission spectrum of the mixed light from the light emitting device of Examples and Comparative Examples are plotted.

Correlated Color Temperature, General Color Rendering Index Ra, Specialty Color Rendering Indices R9 and R12

Using an optical measurement system including a combination of a multichannel spectroscope and an integrating sphere, the correlated color temperature (Tcp; K) of the light emitting device of Examples and Comparative Examples was measured according to JIS Z8725, and the general color rendering index Ra and the specialty color rendering indices R9 and R12 were measured according to JIS Z8726. The results are shown in Table 2 to Table 9.

Relative Emission Intensity (%)

Using a total luminous flux measurement system using an integrating sphere, the emission efficiency (lm/W) expressed as a total luminous flux per unit power of the light emitting device of Examples and Comparative Examples was measured. Based on the emission efficiency of the light emitting device of Comparative Example that uses a light emitting element having an emission peak wavelength at each correlated color temperature of 450 nm, as normalized to 100%, the relative emission efficiency (%) of the light emitting device of the other Examples and Comparative Examples was calculated. The results are shown in Table 2 to Table 9.

TABLE 2

|  | Light Emitting Element Peak Wavelength (nm) | Fluorescent Material | | | |
| --- | --- | --- | --- | --- | --- |
|  |  | Content of First Fluorescent Material (% by mass) | Content of Second Fluorescent Material 1 (% by mass) | Content of Second Fluorescent Material 2 (% by mass) | Content of Third Fluorescent Material (% by mass) |
| Comparative Example 1 | 450 | — | YAG-1 79.9 | YAG-2 14.1 | SCASN-1 6.0 |
| Comparative Example 2 | 405 | — | LAG-1 98.1 | — | SCASN-2 1.9 |
| Comparative Example 3 | 405 | — | Chlorosilicate 56.2 | — | SCASN-2 43.8 |
| Example 1 | 405 | CCA 10.5 | LAG-1 85.9 | — | SCASN-2 3.6 |
| Example 2 | 405 | CCA 12.5 | LAG-1 84.0 | — | SCASN-3 3.5 |
| Example 3 | 405 | CCA 5.1 | LAG-1 91.8 | — | SCASN-2 3.1 |
| Example 4 | 405 | CCA 11.3 | Chlorosilicate 28.3 | LAG-1 42.3 | SCASN-2 18.1 |
| Example 5 | 405 | CCA 5.0 | Chlorosilicate 3.3 | LAG-1 85.4 | SCASN-2 6.3 |
| Example 6 | 405 | CCA 10.0 | Chlorosilicate 10.0 | LAG-1 69.6 | SCASN-2 10.5 |
| Example 7 | 405 | CCA 23.4 | β-SiAlON 56.8 | — | SCASN-1 19.8 |
| Example 8 | 405 | CCA 24.2 | β-SiAlON 58.8 | — | SCASN-3 17.1 |
| Example 9 | 405 | CCA 18.5 | Chlorosilicate 49.8 | — | SCASN-2 31.7 |
| Example 10 | 405 | CCA 28.6 | LSN 64.3 | — | SCASN-2 7.1 |

TABLE 3

| | Light Emitting Device | | | | | | | | | | | |
|---|---|---|---|---|---|---|---|---|---|---|---|---|
| | 380 to 420 nm Emission Amount/ Total Emission Amount (%) | Ratio a (%) | Ratio b (%) | Ratio c (%) | Total of Ratios a + b + c | Correlated Color Temperature (K) | General Color Rendering Index Ra | Specialty Color Rendering Index R9 | Specialty Color Rendering Index R12 | Relative Emission Efficiency (%) | Absolute Value A \|1-ratio a\| | Absolute Value B \|3-ratios a + b + c\| |
| Comparative Example 1 | 0 | 0.5 | 0.6 | 0.4 | 1.5 | 3399 | 82 | 16 | 58 | 100 | 0.5 | 1.5 |
| Comparative Example 2 | 51 | 2.7 | 2.5 | 2.0 | 7.2 | 3503 | 81 | 54 | 7 | 39 | 1.7 | 4.2 |
| Comparative Example 3 | 37 | 1.7 | 1.6 | 1.4 | 4.7 | 3515 | 81 | 71 | 8 | 42 | 0.7 | 1.7 |
| Example 1 | 20 | 1.1 | 1.3 | 1.0 | 3.4 | 3378 | 96 | 75 | 87 | 54 | 0.1 | 0.4 |
| Example 2 | 20 | 1.1 | 1.4 | 1.1 | 3.6 | 3339 | 87 | 14 | 90 | 65 | 0.1 | 0.6 |
| Example 3 | 28 | 1.4 | 1.4 | 1.1 | 4.0 | 3498 | 92 | 66 | 73 | 52 | 0.4 | 1.0 |
| Example 4 | 24 | 1.6 | 1.5 | 1.3 | 4.4 | 3591 | 86 | 67 | 60 | 49 | 0.6 | 1.4 |
| Example 5 | 30 | 1.5 | 1.6 | 1.3 | 4.3 | 3521 | 93 | 94 | 61 | 49 | 0.5 | 1.3 |
| Example 6 | 22 | 1.3 | 1.4 | 1.2 | 3.9 | 3514 | 92 | 91 | 71 | 50 | 0.3 | 0.9 |
| Example 7 | 20 | 1.5 | 1.2 | 1.0 | 3.7 | 3547 | 87 | 65 | 65 | 62 | 0.5 | 0.7 |
| Example 8 | 21 | 1.4 | 1.3 | 1.0 | 3.7 | 3550 | 81 | 17 | 61 | 68 | 0.4 | 0.7 |
| Example 9 | 22 | 1.5 | 1.4 | 1.3 | 4.2 | 3520 | 85 | 64 | 60 | 48 | 0.5 | 1.2 |
| Example 10 | 17 | 1.5 | 1.5 | 1.1 | 4.1 | 3432 | 81 | 24 | 62 | 64 | 0.5 | 1.1 |

Figure 8:
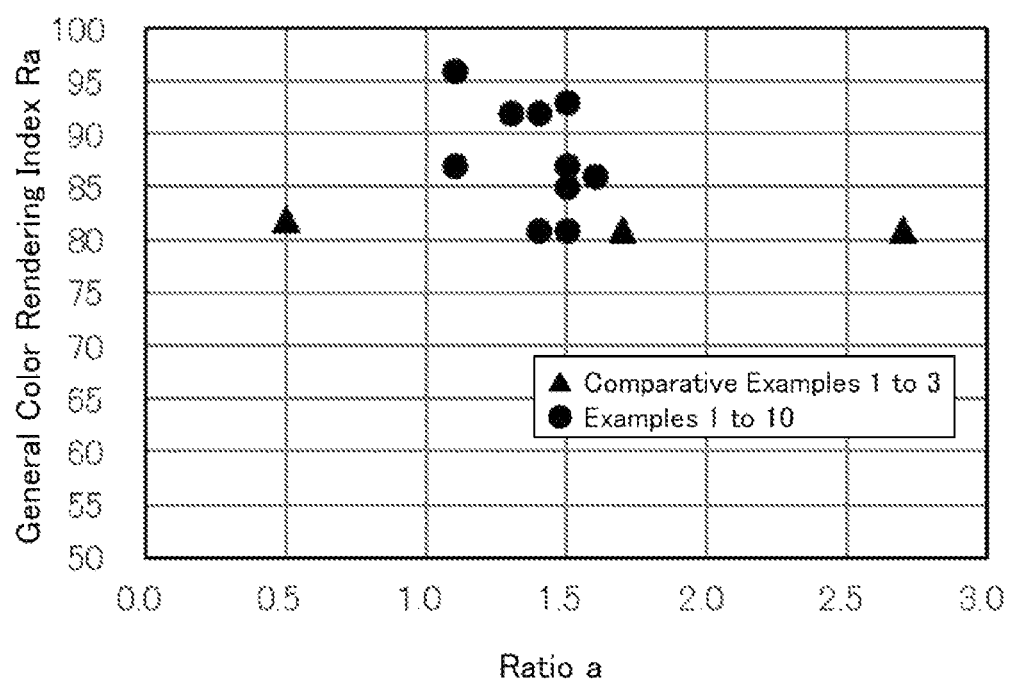
FIG. 8 is a graph plotted between the ratio a obtained from the emission spectrum of mixed light emitted from each of the light emitting devices of Examples 1 to 10 and Comparative Examples 1 to 3 and the general color rendering index Ra of each device.

As shown in Table 3 and FIG. 8, in the light emitting devices of Examples 1 to 10 having a correlated color temperature around 3500 K, the proportion of the integral value over a wavelength range of 380 nm to 420 nm, relative to the integral value over a wavelength range of 380 nm to 780 nm (380 nm to 420 nm emission amount/total emission amount) is 17% to 30%, and the ratio a is 1.1 to 1.6, that is, the light emitting devices emitted mixed light containing a large amount of a light component falling within a wavelength range of 380 nm to 420 nm and having a germicidal effect, and had a sterilization effect. The specialty color rendering index R12 of the light emitting devices of Examples 1 to 10 is 60 or more and is almost equal to the numerical value of the specialty color rendering index R12 of the light emitting device of Comparative Example 1 that uses a light emitting element having an emission peak wavelength at 450 nm, and is larger than the numerical value of the specialty color rendering index R12 of the light emitting devices of Comparative Examples 2 and 3 not using a first fluorescent material. These results verify improved visibility of blue irradiated with the light emitting devices of Examples 1 to 10.

Figure 9:
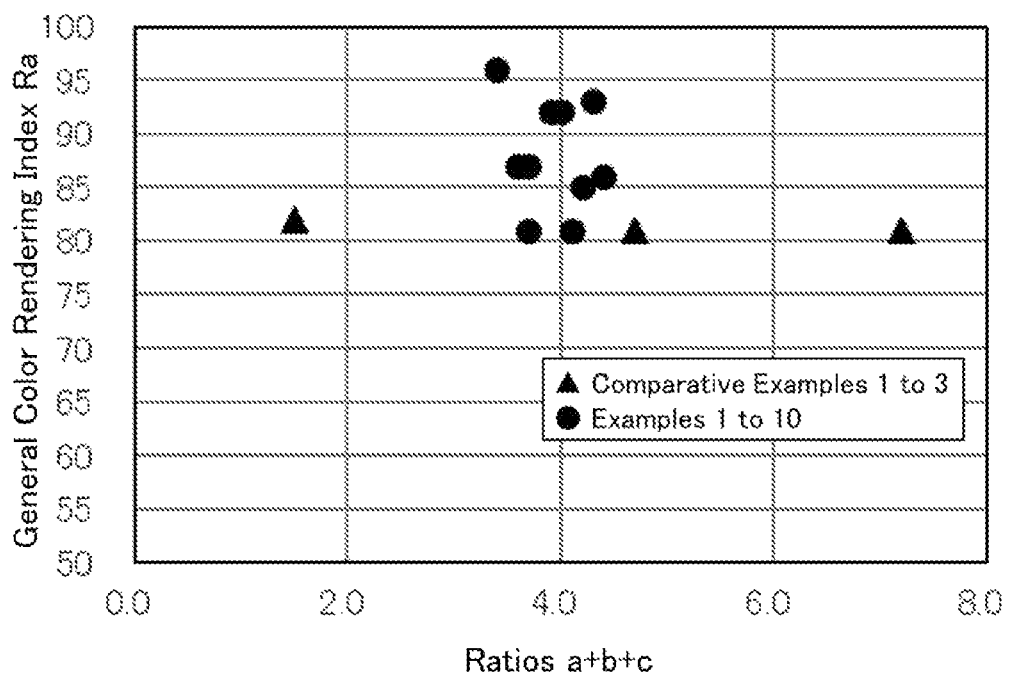
FIG. 9 is a graph plotted between the total of the ratios a, b and c obtained from the emission spectrum of mixed light emitted from each of the light emitting devices of Examples 1 to 10 and Comparative Examples 1 to 3 and the general color rendering index Ra of each device.

As shown in Table 3 and FIG. 9, the total of the ratio a, the ratio b and the ratio c of the light emitting devices of Examples 1 to 10 falls within a range of 3.4 to 4.4, that is, these light emitting devices emitted mixed light containing a blue-violet component having a germicidal effect and containing color components of a blue color component, a green color component, a yellow color component and a red color component in a well-balanced manner. The light emitting devices of Examples 1 to 10 had a color rendering property with a general color rendering index Ra of 80 or more. In general, emission efficiency and color rendering property are in a trade-off relationship, and a light emitting device capable of emitting mixed light having a larger amount of a light component falling within a wavelength range having a germicidal effect is more effective for the sterilization effect, but when the light component in a wavelength range having a germicidal effect is too much, emission of light with a wavelength departing from the peak of a human standard relative luminosity (general spectral luminous efficiency) becomes great to lower the emission efficiency. Consequently, the relative emission efficiency in Examples 1 to 10 was lower than that in Comparative Example 1, but was higher than in Comparative Examples 2 and 3.

As shown in FIG. 10, the absolute value A of a value calculated by subtracting the ratio a, which is derived from the emission spectrum of the light emitting device of Examples 1 to 10, from 1 is not more than 0.6, and it has been found that even the light emitting devices capable of emitting a light component having a germicidal effect can emit mixed light nearer to that from the reference light source at the correlated color temperature of the light emitting devices and having a good balance between the blue light component and the green light component. As shown in FIG. 11, when the absolute value A of a value calculated by subtracting the ratio a, which is derived from the emission spectrum of the light emitting devices of Examples 1, 6 and 9, from 1 is smaller, the average color rendering index Ra of the devices tends to increase. The result demonstrates that even the light emitting devices capable of emitting a blue light having a germicidal effect and having an enhanced sterilization effect can emit mixed light having a good balance between the blue component and the green component and nearer to the reference light source at the correlated color temperature of the light emitting device so far as the absolute value A of a value calculated by subtracting the ratio a from 1 is small, and consequently, the light emitting devices of the type can have an increased general color rendering index Ra that indicates comfortable use of the devices in human life environments.

As shown in FIG. 12, the absolute value B of a value calculated by subtracting the total of the ratio a, the ratio b and the ratio c, which is derived from the emission spectrum of the light emitting device of Examples 1 to 10, from 3 is less than 1.5, and it has been found that even the light emitting devices capable of emitting a light component having a germicidal effect can emit mixed light nearer to that from the reference light source at the correlated color temperature of the light emitting devices and having a good balance between the blue light component, the green light component, the yellow light component and the red light component. As shown in FIG. 13, when the absolute value B of a value calculated by subtracting the total of the ratio a, the ratio b and the ration c, which is derived from the emission spectrum of the light emitting devices of Examples 1, 6 and 9, from 3 is smaller, the average color rendering index Ra of the devices tends to increase. The result demonstrates that even the light emitting devices capable of emitting a blue light having a germicidal effect and having an enhanced sterilization effect can emit mixed light having a good balance between the blue component, the green component, the yellow component and the red component and nearer to the reference light source at the correlated color temperature of the light emitting device so far as the absolute value B of a value calculated by subtracting the total of the ratio a, the ratio b and the ratio c from 3 is small, and consequently, the light emitting devices of the type can have an increased general color rendering index Ra that indicates comfortable use of the devices in human life environments.

As shown in Table 3, in the light emitting device of Comparative Example 1, the proportion of the integral value over a wavelength range of 380 nm to 420 nm having a germicidal effect is 0%, that is, the device does not have a sterilization effect. In the light emitting devices of Comparative Examples 2 and 3, the proportion of the emission amount in a range of 380 nm to 420 nm to the total emission amount (380 nm to 420 nm emission amount/total emission amount) is not less than 15%, but the ratio a is more than 1.6 and is large, that is, the mixed light from the devices lost color balance. In the light emitting devices of Comparative Examples 2 and 3, the ratio a is more than 1.6 and is large, and the specialty color rendering index R12 indicating the visibility of blue is low.

Figure 14:
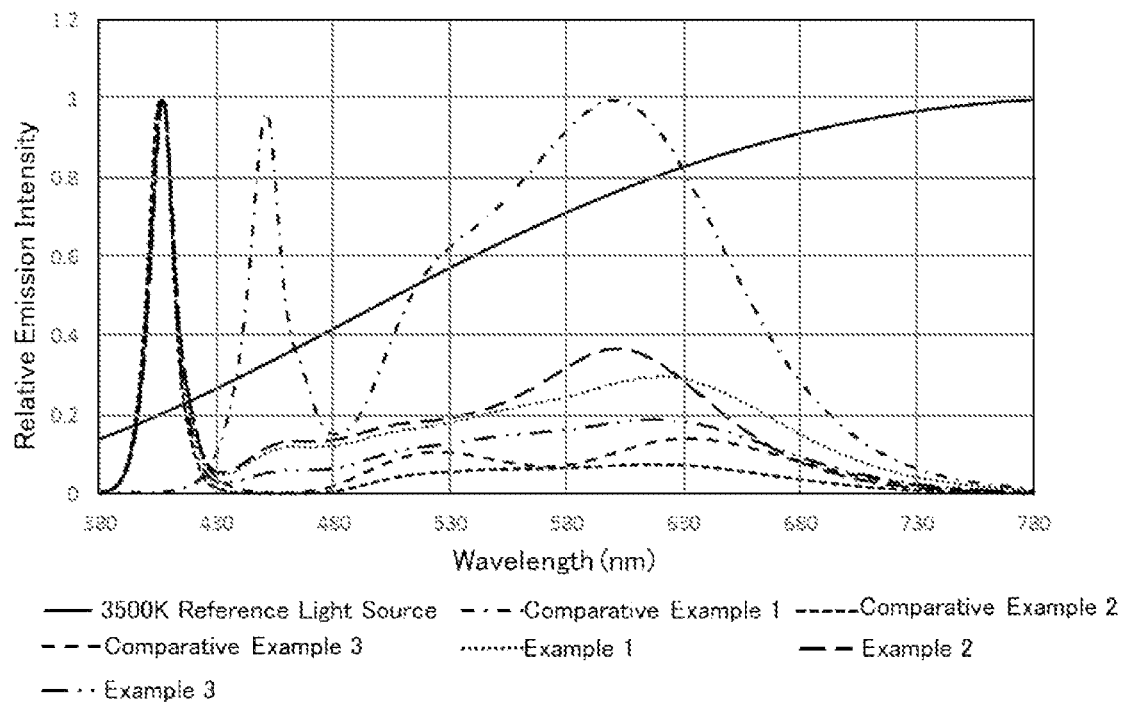
FIG. 14 is a graph showing an emission spectrum of the light emitting device of Examples 1 to 3 and Comparative Examples 1 to 3 at a correlated color temperature around 3500 K, and an emission spectrum of a reference light source (complete radiator) at a correlated color temperature 3500 K.

As shown in FIG. 14, in the emission spectrum (spectral distribution) of each light emitting device of Examples 1 to 3, the light emitting element has an emission peak wavelength within a range of 380 nm to 420 nm, and emits light in a wavelength range having a germicidal effect, and as compared with the emission spectrum of the light emitting devices of Comparative Examples 2 and 3, the emission spectrum of the devices of Examples 1 to 3 is nearer to the emission spectrum of the reference light source in a wavelength range of 430 nm to 680 nm, that is, the devices of Examples 1 to 3 emitted mixed light having a good color balance.

Figure 15:
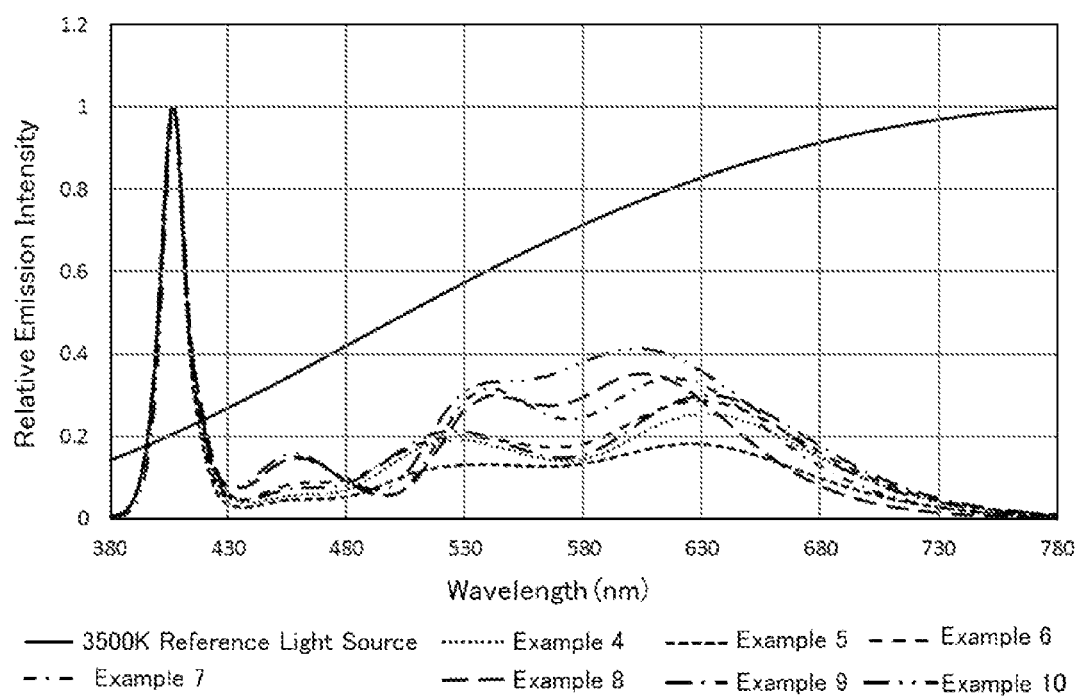
FIG. 15 is a graph showing an emission spectrum of the light emitting device of Examples 4 to 10 at a correlated color temperature around 3500 K, and an emission spectrum of a reference light source (complete radiator) at a correlated color temperature 3500 K.

As shown in FIG. 15, in the emission spectrum (spectral distribution) of each light emitting device of Examples 4 to 10, the light emitting element has an emission peak wavelength within a range of 380 nm to 420 nm, and emits light in a wavelength range having a germicidal effect, and the emission spectrum of the devices of Examples 4 to 10 is nearer to the emission spectrum of the reference light source in a wavelength range of 430 nm to 680 nm, that is, the devices of Examples 4 to 10 emitted mixed light having a good color balance.

Example 11

A light emitting device of Example 11 was produced in the same manner as in Example 1, except that the kind of the first fluorescent material, the second fluorescent material and the third fluorescent material and the content of each fluorescent material relative to the total mass of the fluorescent materials were changed as in Table 4 and the first fluorescent material, the second fluorescent material and the third fluorescent material were blended in such a manner that the correlated color temperature of the mixed light of the light from the light emitting element 10 and the light from the fluorescent material 70 containing the first fluorescent material, the second fluorescent material and the third fluorescent material could be around 4000 K.

Comparative Example 4

A light emitting device of Comparative Example 4 was produced in the same manner as in Example 11, except that a light emitting element having an emission peak wavelength of 450 nm was used, the first fluorescent material was not used, and the second fluorescent material and the third fluorescent material were blended in such a manner that the kind of the second fluorescent material and the third fluorescent material and the content of each fluorescent material relative to the total mass of the fluorescent materials were changed as in Table 4.

Comparative Example 5

A light emitting device of Comparative Example 5 was produced in the same manner as in Example 11, except that the first fluorescent material was not used, and the second fluorescent material and the third fluorescent material were blended in such a manner that the kind of the second fluorescent material and the third fluorescent material and the content of each fluorescent material relative to the total mass of the fluorescent materials were as in Table 4.

TABLE 4

|  | Light Emitting Element Peak Wavelength (nm) | Fluorescent Material | | | |
|---|---|---|---|---|---|
|  |  | Content of First Fluorescent Material (% by mass) | Content of Second Fluorescent Material 1 (% by mass) | Content of Second Fluorescent Material 2 (% by mass) | Content of third Fluorescent Material (% by mass) |
| Comparative Example 4 | 450 | — | LAG-1 95.6 | — | SCASN-1 4.5 |
| Comparative Example 5 | 405 | — | LAG-1 98.5 | — | SCASN-1 1.5 |
| Example 11 | 405 | CCA 10.0 | YAG-1 73.7 | YAG-2 13.0 | SCASN-1 3.2 |

TABLE 5

| | Light Emitting Device | | | | | | | | | | |
|---|---|---|---|---|---|---|---|---|---|---|---|
| | 380 to 420 nm Emission Amount/ Total Emission Amount (%) | Ratio a (%) | Ratio b (%) | Ratio c (%) | Total of Ratios a + b + c | Correlated Color Temperature (K) | General Color Rendering Index Ra | Specialty Color Rendering Index R9 | Specialty Color Rendering Index R12 | Relative Emission Efficiency (%) | Absolute Value A \|1-ratio a\| | Absolute Value B \|3-ratios a + b + c\| |
| Comparative Example 4 | 0 | 0.5 | 0.5 | 0.5 | 1.6 | 4099 | 85 | 29 | 59 | 100 | 0.5 | 1.4 |
| Comparative Example 5 | 57 | 2.6 | 2.5 | 2.3 | 7.4 | 4129 | 78 | 29 | 0 | 35 | 1.6 | 4.4 |
| Example 11 | 30 | 1.4 | 1.6 | 1.4 | 4.4 | 3902 | 90 | 42 | 75 | 49 | 0.4 | 1.4 |

Figure 16:
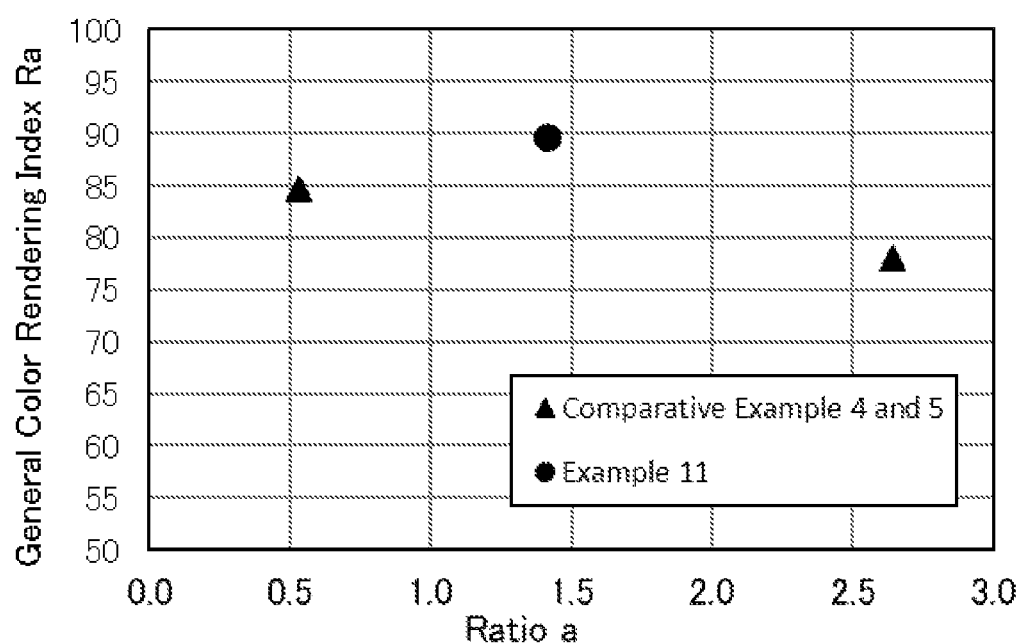
FIG. 16 is a graph plotted between the ratio a obtained from the emission spectrum of mixed light emitted from each of the light emitting devices of Example 11 and Comparative Examples 4 and 5 and the general color rendering index Ra of each device.

As shown in Table 5 and FIG. 16, in the light emitting device of Example 11 having a correlated color temperature around 4000 K, the proportion of the emission amount in a range of 380 nm to 420 nm relative to the total emission amount (380 nm to 420 nm emission amount/total emission amount) is 30%, and the ratio a is 1.4, that is, the light emitting device emitted mixed light containing much light that falls within a wavelength range of 380 nm to 420 nm having a germicidal effect, and had a sterilization effect. The light emitting device of Example 11 has a specialty color rendering index R12, which indicates visibility of blue, of 75, that is, the specialty color rendering index R12 of the light emitting device of Example 11 is not less than 60 and is larger than the numerical value of the specialty color rendering index R12 in Comparative Example 4 that uses a light emitting element having an emission peak wavelength at 450 nm, and the result verifies improved visibility of blue irradiated with the light emitting device of Example 11.

Figure 17:
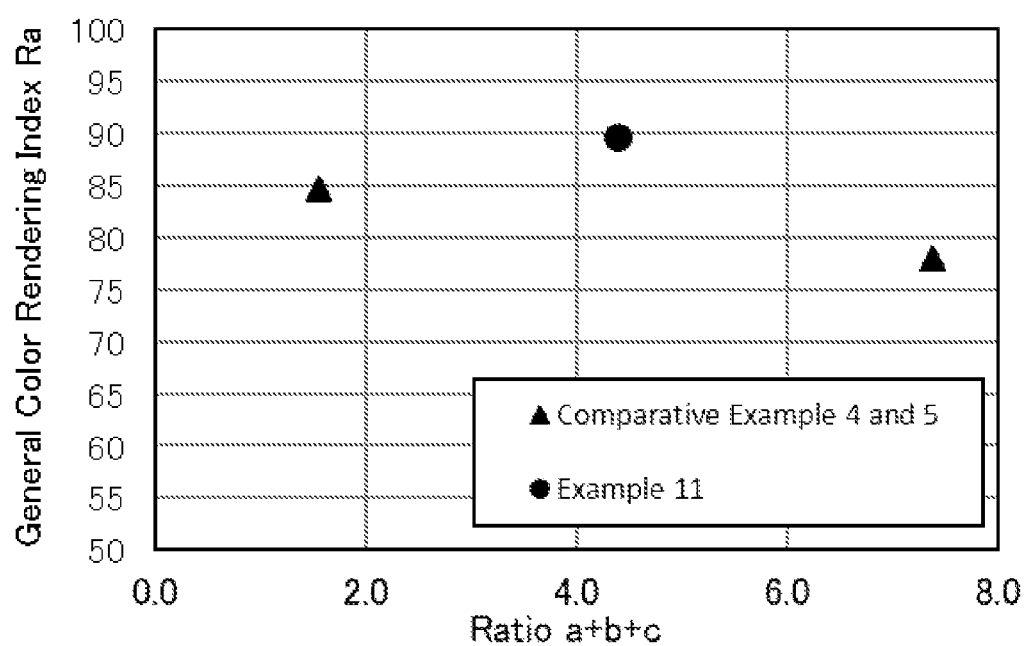
FIG. 17 is a graph plotted between the total of the ratios a, b and c obtained from the emission spectrum of mixed light emitted from each of the light emitting devices of Example 11 and Comparative Examples 4 and 5 and the general color rendering index Ra of each device.

As shown in Table 5 and FIG. 17, in the light emitting device of Example 11, the total of the ratio a, the ratio b and the ratio c is 4.4, that is, the mixed light emitted from the device contains a blue-violet color component having a germicidal effect and is well balanced in point of the blue component, the green component, the yellow component and the red component. The light emitting device of Example 11 has a general color rendering index Ra of 90 and has a high-level color rendering property. Emission efficiency and color rendering property are in a trade-off relationship, and a light emitting device capable of emitting mixed light having a larger amount of a light component falling within a wavelength range having a germicidal effect is more effective for the sterilization effect, but when the light component in a wavelength range having a germicidal effect is too much, emission of light with a wavelength departing from the peak of a human standard relative luminosity (general spectral luminous efficiency) becomes great to lower the emission efficiency. Consequently, the relative emission efficiency in Example 11 was lower than that in Comparative Example 4, but was higher than that in Comparative Example 5.

As shown in Table 5, in the light emitting device of Comparative Example 4, the proportion of the integral value over a wavelength range of 380 nm to 420 nm having a germicidal effect is 0%, and the ratio a is 0.5 and is low, that is, the light emitting device of Comparative Example 4 does not have a sterilization effect. In the light emitting device of Comparative Example 5, the proportion of the emission amount in a range of 380 nm to 420 nm relative to the total emission amount (380 nm to 420 nm emission amount/total emission amount) is not less than 15%, but the ratio a is more than 1.6 and is large, and the mixed light from the device lost color balance. In the light emitting device of Comparative Example 5, the ratio a is 2.6 and is large, the specialty color rendering index R12 that indicates the visibility of blue is low, and the relative emission efficiency is low.

Figure 18:
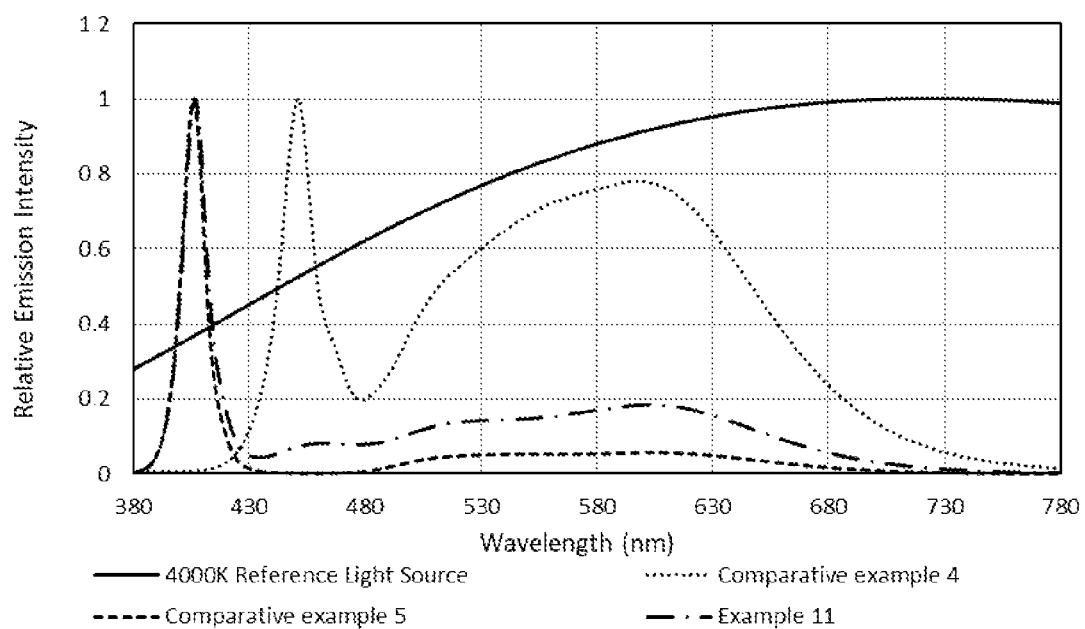
FIG. 18 is a graph showing an emission spectrum of the light emitting device of Example 11 and Comparative Examples 4 and 5 at a correlated color temperature around 4000 K, and an emission spectrum of a reference light source (complete radiator) at a correlated color temperature 4000 K.

As shown in FIG. 18, in the light emitting device of Example 11, the light emitting element has an emission peak wavelength in a wavelength range of 380 nm to 420 nm in the emission spectrum (spectral distribution), that is, the light emitting element emits light falling within a wavelength range having a germicidal effect, and as compared with the emission spectrum in Comparative Example 5, the emission spectrum of the device of Example 11 is nearer to the emission spectrum of the reference light source in a wavelength range of 430 nm to 680 nm, that is, the device of Example 11 emitted mixed light having well-balanced color components.

Example 12

A light emitting device of Example 12 was produced in the same manner as in Example 1 except that the kind of the first fluorescent material, the second fluorescent material and the third fluorescent material and the content of each fluorescent material relative to the total mass of the fluorescent materials were changed as in Table 6 and the first fluorescent material, the second fluorescent material and the third fluorescent material were blended in such a manner that the correlated color temperature of the mixed light of the light from the light emitting element 10 and the light from the fluorescent material 70 containing the first fluorescent material, the second florescent material and the third fluorescent material could be around 6500 K.

Comparative Example 6

A light emitting device of Comparative Example 6 was produced in the same manner as in Example 12 except that a light emitting element having an emission peak wavelength of 450 nm was used, the first fluorescent material was not used, the kind of the second fluorescent material and the third fluorescent material and the content of each fluorescent material relative to the total mass of the fluorescent materials were changed as in Table 6, and the second fluorescent material and the third fluorescent material were blended.

Comparative Example 7

A light emitting device of Comparative Example 7 was produced in the same manner as in Example 12, except that the first fluorescent material was not used, and the second fluorescent material and the third fluorescent material were blended in such a manner that the kind of the second fluorescent material and the third fluorescent material and the content of each fluorescent material relative to the total mass of the fluorescent materials were as in Table 6.

and the red component. The light emitting device of Example 12 has a general color rendering index Ra of 97 and has a high-level color rendering property. Emission efficiency and color rendering property are in a trade-off relationship, and a light emitting device capable of emitting mixed light having a larger amount of a light component falling within a wavelength range having a germicidal effect is more effective for the sterilization effect, but when the light component in a wavelength range having a germicidal effect is too much, emission of light with a wavelength

TABLE 6

| | Light Emitting Element Peak Wavelength (nm) | Fluorescent Material | | | |
|---|---|---|---|---|---|
| | | Content of First Fluorescent Material (% by mass) | Content of Second Fluorescent Material 1 (% by mass) | Content of Second Fluorescent Material 2 (% by mass) | Content of Third Fluorescent Material (% by mass) |
| Comparative Example 6 | 450 | — | LAG-1 97.0 | — | SCASN-1 3.0 |
| Comparative Example 7 | 405 | — | LAG-1 99.5 | — | SCASN-1 0.5 |
| Example 12 | 405 | CCA 25.0 | LAG-1 72.0 | — | SCASN-2 3.0 |

TABLE 7

| | Light Emitting Device | | | | | | | | | | | |
|---|---|---|---|---|---|---|---|---|---|---|---|---|
| | 380 to 420 nm Emission Amount/ Total Emission Amount (%) | Ratio a (%) | Ratio b (%) | Ratio c (%) | Total of Ratios a + b + c | Correlated Color Temperature (K) | General Color Rendering Index Ra | Specialty Color Rendering Index R9 | Specialty Color Rendering Index R12 | Relative Emission Efficiency (%) | Absolute Value A \|1-ratio a\| | Absolute Value B \|3-ratios a + b + c\| |
| Comparative Example 6 | 0 | 0.4 | 0.4 | 0.4 | 1.2 | 6664 | 76 | −4 | 42 | 100 | 0.6 | 1.8 |
| Comparative Example 7 | 70 | 1.8 | 1.8 | 1.5 | 5.1 | 6730 | 68 | 6 | −22 | 24 | 0.8 | 2.1 |
| Example 12 | 24 | 1.0 | 0.9 | 1.0 | 2.8 | 6657 | 97 | 97 | 88 | 44 | 0.0 | 0.2 |

Figure 19:
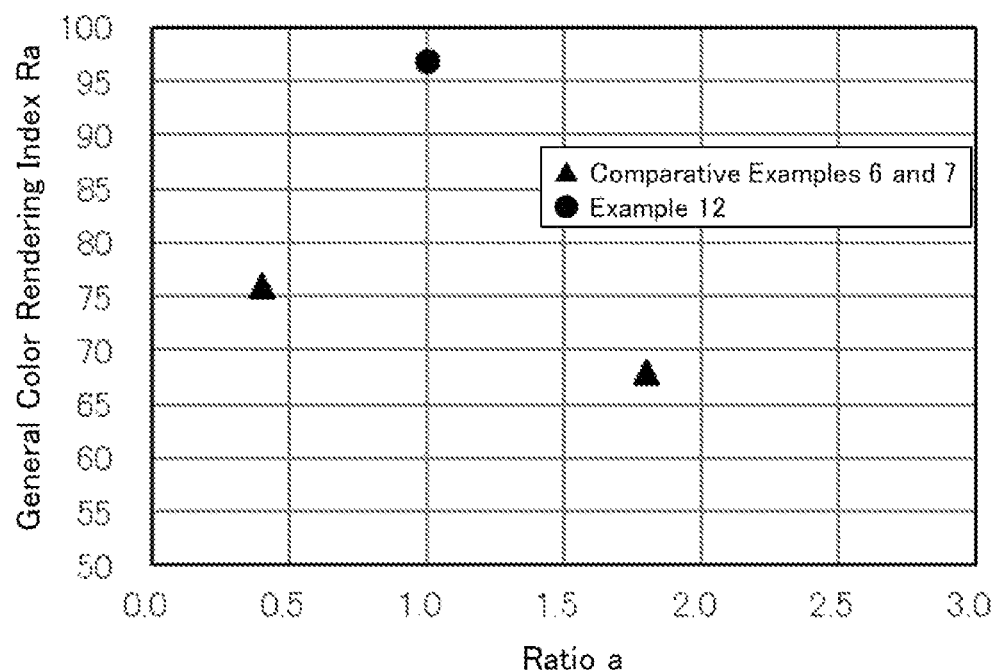
FIG. 19 is a graph plotted between the ratio a obtained from the emission spectrum of mixed light emitted from each of the light emitting devices of Example 12 and Comparative Examples 6 and 7 and the general color rendering index Ra of each device.

As shown in Table 7 and FIG. 19, in the light emitting device of Example 12 having a correlated color temperature around 6500 K, the proportion of the emission amount in a range of 380 nm to 420 nm relative to the total emission amount (380 nm to 420 nm emission amount/total emission amount) is 24%, and the ratio a is 1.0, that is, the light emitting device emitted mixed light containing much light that falls within a wavelength range of 380 nm to 420 nm having a germicidal effect, and had a sterilization effect. The light emitting device of Example 12 has a specialty color rendering index R12 of not less than 60 and is larger than the numerical value of the specialty color rendering index R12 in Comparative Example 6 that uses a light emitting element having an emission peak wavelength at 450 nm, and the result verifies improved visibility of blue irradiated with the light emitting device of Example 12.

Figure 20:
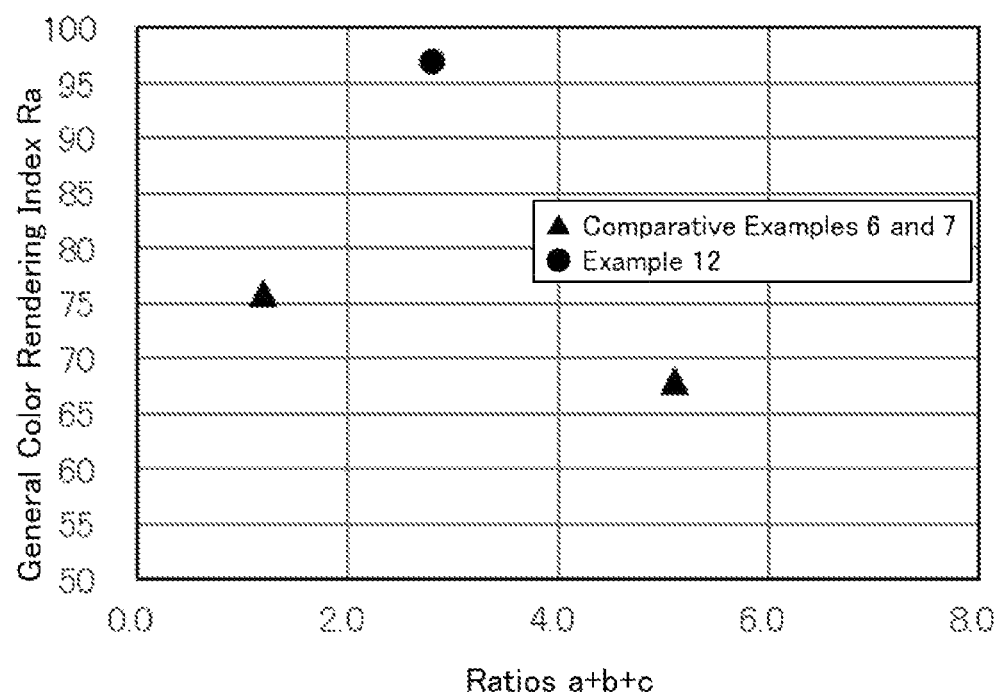
FIG. 20 is a graph plotted between the total of the ratios a, b and c obtained from the emission spectrum of mixed light emitted from each of the light emitting devices of Example 12 and Comparative Examples 6 and 7 and the general color rendering index Ra of each device.

As shown in Table 7 and FIG. 20, in the light emitting device of Example 12, the total of the ratio a, the ratio b and the ratio c is 2.8, that is, the mixed light emitted from the device contains a blue-violet color component having a germicidal effect and is well balanced in point of the blue component, the green component, the yellow component departing from the peak of a human standard relative luminosity (general spectral luminous efficiency) becomes great to lower the emission efficiency. Consequently, the relative emission efficiency in Example 12 was lower than that in Comparative Example 6, but was higher than that in Comparative Example 7.

As shown in Table 7, in the light emitting device of Comparative Example 6, the proportion of the integral value over a wavelength range of 380 nm to 420 nm having a germicidal effect is 0%, and the ratio a is 0.4 and is low, that is, the light emitting device of Comparative Example 6 does not have a sterilization effect. In the light emitting device of Comparative Example 7, the proportion of the emission amount in a range of 380 nm to 420 nm relative to the total emission amount (380 nm to 420 nm emission amount/total emission amount) is 70%, and the ratio a is 1.8 and is large, and the mixed light from the device lost color balance. In the light emitting device of Comparative Example 7, the specialty color rendering index R12 that indicates the visibility of blue is low, and the relative emission efficiency is low.

As shown in FIG. 21, in the light emitting device of Example 12, the light emitting element has an emission peak wavelength in a range of 380 nm to 420 nm in the emission spectrum (spectral distribution), that is, the light emitting element emits light falling within a wavelength range having a germicidal effect, and as compared with the emission spectrum in Comparative Example 7, the emission spectrum of the device of Example 12 is nearer to the emission spectrum of the reference light source in a wavelength range of 430 nm to 680 nm, that is, the device of Example 12 emitted mixed light having well-balanced color components.

Examples 13 and 14

Light emitting devices of Examples 13 and 14 were produced in the same manner as in Example 1 except that the kind of the first fluorescent material, the second fluorescent material and the third fluorescent material and the content of each fluorescent material relative to the total mass of the fluorescent materials were changed as in Table 8, and the first fluorescent material, the second fluorescent material and the third fluorescent materials were blended in such a manner that the correlated color temperature of the mixed light of the light from the light emitting element 10 and the light from the fluorescent material 70 containing the first fluorescent material, the second fluorescent material and the third fluorescent material could be around 2700 K.

Comparative Example 8

A light emitting device of Comparative Example 8 was produced in the same manner as in Example 12 except that a light emitting element having an emission peak wavelength of 450 nm was used, the first fluorescent material was not used, the kind of the second fluorescent material and the third fluorescent material and the content of each fluorescent material relative to the total mass of the fluorescent materials were changed as in Table 8, and the second fluorescent material and the third fluorescent material were blended.

Comparative Example 9

A light emitting device of Comparative Example 9 was produced in the same manner as in Example 12, except that the first fluorescent material was not used, and the second fluorescent material and the third fluorescent material were blended in such a manner that the kind of the second fluorescent material and the third fluorescent material and the content of each fluorescent material relative to the total mass of the fluorescent materials were as in Table 8.

TABLE 8

| | Light Emitting Element Peak Wavelength (nm) | Fluorescent Material | | | |
|---|---|---|---|---|---|
| | | Content of First Fluorescent Material (% by mass) | Content of Second Fluorescent Material 1 (% by mass) | Content of Second Fluorescent Material 2 (% by mass) | Content of Third Fluorescent Material (% by mass) |
| Comparative Example 8 | 450 | — | LAG-1 92.8 | — | SCASN-1 7.3 |
| Comparative Example 9 | 405 | — | LAG-1 97.2 | — | SCASN-1 2.8 |
| Example 13 | 405 | CCA 7.8 | LAG-1 87.8 | — | SCASN-2 4.4 |
| Example 14 | 405 | CCA 8.7 | LAG-1 87.2 | — | SCASN-3 4.1 |

TABLE 9

| | Light Emitting Device | | | | | | | | | | |
|---|---|---|---|---|---|---|---|---|---|---|---|
| | 380 to 420 nm Emission Amount/ Total Emission Amount (%) | Ratio a (%) | Ratio b (%) | Ratio c (%) | Total of Ratios a + b + c | Correlated Color Temperature (K) | General Color Rendering Index Ra | Specialty Color Rendering Index R9 | Specialty Color Rendering Index R12 | Relative Emission Efficiency (%) | Absolute Value A \|1-ratio a\| | Absolute Value B \|3-ratios a + b + c\| |
| Comparative Example 8 | 0 | 0.6 | 0.7 | 0.4 | 1.7 | 2775 | 85 | 25 | 74 | 100 | 0.4 | 1.3 |
| Comparative Example 9 | 44 | 2.7 | 3.0 | 1.6 | 7.3 | 2814 | 86 | 41 | 27 | 44 | 1.7 | 4.3 |
| Example 13 | 16 | 1.3 | 1.3 | 0.7 | 3.3 | 2894 | 94 | 66 | 84 | 54 | 0.3 | 0.3 |
| Example 14 | 16 | 1.3 | 1.5 | 0.8 | 3.5 | 2770 | 81 | −1 | 85 | 66 | 0.3 | 0.5 |

Figure 22:
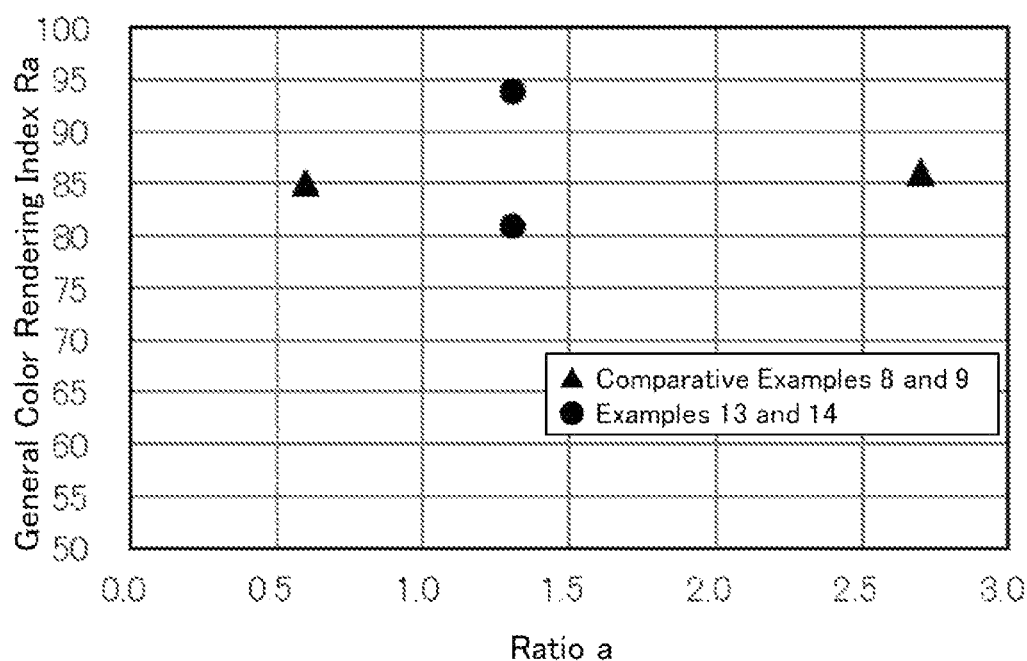
FIG. 22 is a graph plotted between the ratio a obtained from the emission spectrum of mixed light emitted from each of the light emitting devices of Examples 13 and 14 and Comparative Examples 8 and 9 and the general color rendering index Ra of each device.

As shown in Table 9 and FIG. 22, in the light emitting devices of Examples 13 and 14 having a correlated color temperature around 2700 K, the proportion of the emission amount in a range of 380 nm to 420 nm relative to the total emission amount (380 nm to 420 nm emission amount/total emission amount) is 16%, and the ratio a is 1.3, that is, the light emitting devices emitted mixed light containing much light that falls within a wavelength range of 380 nm to 420 nm having a germicidal effect, and had a sterilization effect. The light emitting devices of Examples 13 and 14 have a specialty color rendering index R12 of not less than 60 and is larger than the numerical value of the specialty color rendering index R12 in Comparative Example 8 that uses a light emitting element having an emission peak wavelength at 450 nm, and the result verifies improved visibility of blue irradiated with the light emitting devices of Examples 13 and 14.

Figure 23:
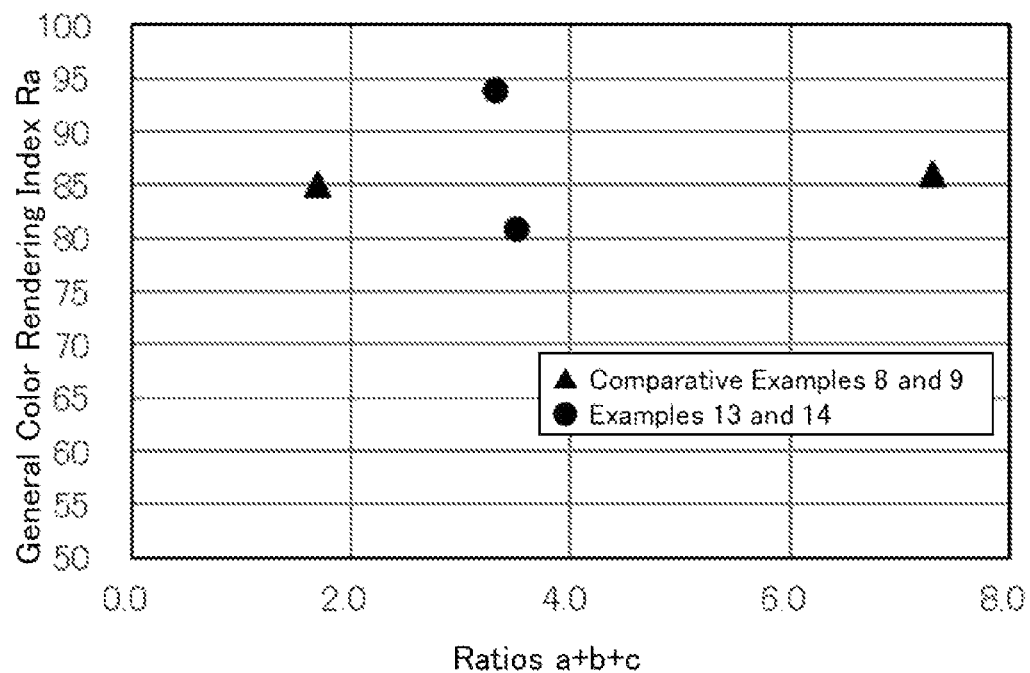
FIG. 23 is a graph plotted between the total of the ratios a, b and c obtained from the emission spectrum of mixed light emitted from each of the light emitting devices of Examples 13 and 14 and Comparative Examples 8 and 9 and the general color rendering index Ra of each device.

As shown in Table 9 and FIG. 23, in the light emitting devices of Examples 13 and 14, the total of the ratio a, the ratio b and the ratio c is 3.3 or 3.5, that is, the mixed light emitted from the devices contains a blue-violet color component having a germicidal effect and is well balanced in point of the blue component, the green component, the yellow component and the red component. The light emitting device of Example 13 has a general color rendering index Ra of 94 and has a high-level color rendering property. The light emitting device of Example 14 has a general color rendering index Ra of 81 and also has a high-level color rendering property. Emission efficiency and color rendering property are in a trade-off relationship, and a light emitting device capable of emitting mixed light having a larger amount of a light component falling within a wavelength range having a germicidal effect is more effective for the sterilization effect, but when the light component in a wavelength range having a germicidal effect is too much, emission of light with a wavelength departing from the peak of a human standard relative luminosity (general spectral luminous efficiency) becomes great to lower the emission efficiency. Consequently, the relative emission efficiency in Examples 13 and 14 was lower than that in Comparative Example 8, but was higher than that in Comparative Example 9.

As shown in Table 9, in the light emitting device of Comparative Example 8, the proportion of the integral value over a wavelength range of 380 nm to 420 nm having a germicidal effect is 0%, and the ratio a is 0.6 and is low, that is, the light emitting device of Comparative Example 8 does not have a sterilization effect. In the light emitting device of Comparative Example 9, the proportion of the emission amount in a range of 380 nm to 420 nm relative to the total emission amount (380 nm to 420 nm emission amount/total emission amount) is 44%, and the ratio a is 2.7 and is large, and the mixed light from the device lost color balance. In the light emitting device of Comparative Example 9, the specialty color rendering index R12 that indicates the visibility of blue is low, and the relative emission efficiency is low.

Figure 24:
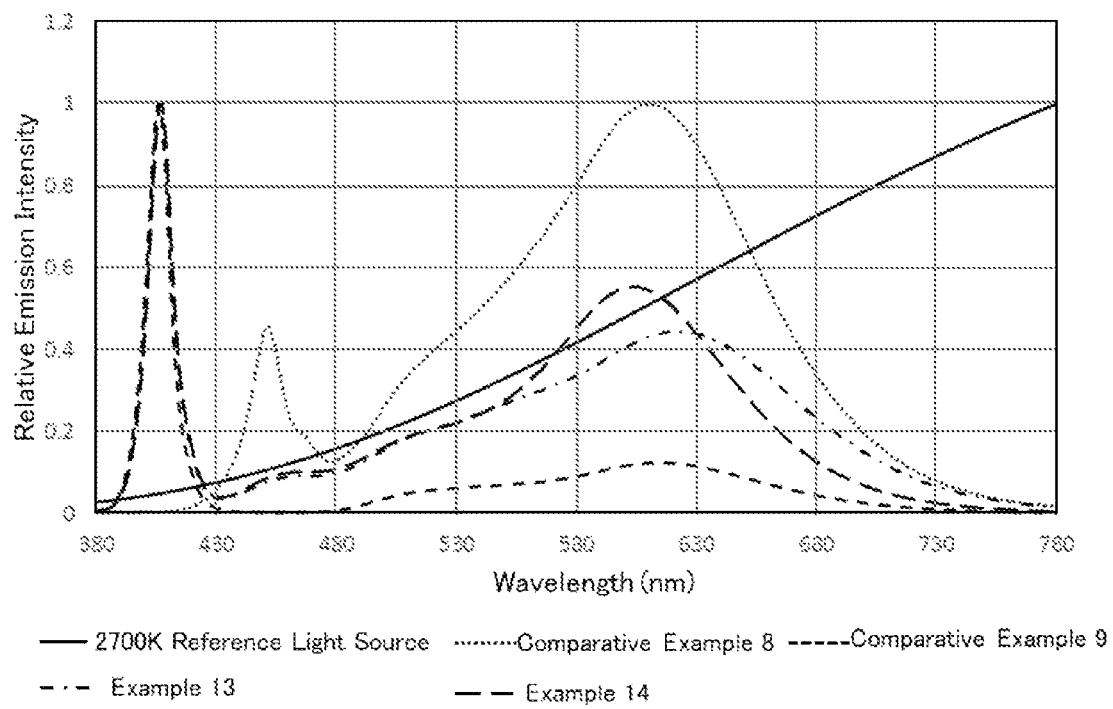
FIG. 24 is a graph showing an emission spectrum of the light emitting device of Examples 13 and 14 and Comparative Examples 8 and 9 at a correlated color temperature around 2700 K, and an emission spectrum of a reference light source (complete radiator) at a correlated color temperature 2700 K.

As shown in FIG. 24, in the light emitting devices of Examples 13 and 14, the light emitting element has an emission peak wavelength in a wavelength range of 380 nm to 420 nm in the emission spectrum (spectral distribution), that is, the light emitting element emits light falling within a wavelength range having a germicidal effect, and as compared with the emission spectrum in Comparative Example 9, the emission spectrum of the device of Examples 13 and 14 is nearer to the emission spectrum of the reference light source in a wavelength range of 430 nm to 680 nm, that is, the devices of Examples 13 and 14 emitted mixed light having well-balanced color components.

The light emitting device of one embodiment of the present disclosure can be used as illumination devices, especially as illumination devices for medical use illumination devices for foods that are required to have a sterilization effect of suppressing growth of bacteria in use environments.

The invention claimed is:
1. A method for producing a light emitting device, comprising:
    preparing
        a fluorescent member composition containing a resin, a first fluorescent material, a second fluorescent material, and a third fluorescent material, the first fluorescent material, the second fluorescent material, and the third fluorescent material each emitting light as excited by light emitted from a light emitting element having a light emission peak wavelength in a range of 380 nm to 420 nm, and being mixed to make a content of the first fluorescent material of 1.0% by mass or more and 50.0% by mass or less, a content of the second fluorescent material of 45.0% or more and 99.0% by mass or less, and a content of the third fluorescent material of 0% by mass or more and 50.0% by mass or less, relative to the total mass of the first fluorescent material, the second fluorescent material, and the third fluorescent material, and to make the light emitting device having a spectral distribution having a proportion of an integral value over a wavelength range of 380 nm to 420 nm of 15% or more when an integral value over a wavelength range of 380 nm to 780 nm is normalized to 100%, and
        a molded body for mounting the light emitting element, and
    mounting the light emitting element on the molded body, and then arranging and curing the fluorescent member composition on the light emitting element, so as to form a fluorescent member,
    the first fluorescent material containing at least one fluorescent material selected from the group consisting of a fluorescent material having a composition represented by the following formula (I) and a fluorescent material having a composition represented by the following formula (II):

$$(Ca,Sr,Ba,Mg)_{10}(PO_4)_6(F,Cl,Br,I)_2:Eu \quad (I)$$

$$(Ba,Sr,Ca)_3MgSi_2O_8:Eu \quad (II),$$

the second fluorescent material containing at least one fluorescent material selected from the group consisting of a fluorescent material having a composition represented by the following formula (III), a fluorescent material having a composition represented by the following formula (IV), a fluorescent material having a composition represented by the following formula (V), a fluorescent material having a composition represented by the following formula (VI), and a fluorescent material having a composition represented by the following formula (VII):

$$(Lu,Y,Gd,Tb)_3(Al,Ga)_5O_{12}:Ce \quad (III)$$

$$(Ca,Sr,Ba)_8MgSi_4O_{16}(F,Cl,Br)_2:Eu \quad (IV)$$

$$Si_{6-z}Al_zO_zN_{8-z}:Eu(0<z<4.2) \quad (V)$$

$$(La,Y,Gd)_3(Al,Si)_6N_{11}:Ce \quad (VI)$$

$$(Ba,Sr,Ca,Mg)_2SiO_4:Eu \quad (VII),$$

the third fluorescent material containing at least one fluorescent material selected from the group consisting of a fluorescent material having a composition represented by the following formula (VIII), a fluorescent material having a composition represented by the following formula (IX), and a fluorescent material having a composition represented by the following formula (X):

$(Sr,Ca)AlSiN_3:Eu$ (VIII)

$(Ca,Sr,Ba)_2Si_5N_8:Eu$ (IX)

$(Sr,Ca)LiAl_3N_4:Eu$ (X), wherein
the first fluorescent material contains a fluorescent material having a composition represented by the following formula (I'):

$Ca_{10}(PO_4)_6Cl_2:Eu$ (I'), the second fluorescent material contains at least one fluorescent material selected from the group consisting of a fluorescent material having a composition represented by the following formula (III') and a fluorescent material having a composition represented by the following formula (V):

$(Lu,Y)_3(Al,Ga)_5O_{12}:Ce$ (III')

$Si_{6-z}Al_zO_zN_{8-z}:Eu(0<z<4.2)$ (V), and the third fluorescent material contains a fluorescent material having a composition represented by the following formula (VIII'):

$(Sr,Ca)AlSiN_3:Eu$ (VIII').

2. The method for producing a light emitting device according to claim 1, wherein the light emitting element has a light emission peak wavelength in a range of 400 nm to 410 nm.

3. The method for producing a light emitting device according to claim 1, wherein
the first fluorescent material has an emission peak wavelength in a range of 430 nm to less than 485 nm as excited by the light from the light emitting element,
the second fluorescent material has an emission peak wavelength in a range of 485 nm to less than 610 nm as excited by the light from the light emitting element, and
the third fluorescent material has an emission peak wavelength in a range of 610 nm to 780 nm as excited by the light from the light emitting element.

4. The method for producing a light emitting device according to claim 1, wherein the light emitting device has a spectral distribution having a proportion of an integral value over a wavelength range of 380 nm to 420 nm of 35% or less when an integral value over a wavelength range of 380 nm to 780 nm is normalized to 100%.

5. The method for producing a light emitting device according to claim 1, wherein the light emitting device emits light having a general color rendering index Ra of 80 or more, or the light emitting device emits light having a specialty color rendering index R12 of 50 or more.

6. The method for producing a light emitting device according to claim 1, wherein the light emitting device emits light having a specialty color rendering index R9 of 10 or more.

7. The method for producing a light emitting device according to claim 1, wherein the method further comprises:

preparing a reflective member composition containing an oxide having a reflectance at 405 nm of 50% or more and a resin, and arranging and curing the reflective member composition in the molded body to expose a side surface of the light emitting element mounted on the molded body out of the reflective member composition, so as to form a reflective member.

8. The method for producing a light emitting device according to claim 7, wherein the fluorescent member composition is arranged on top of the light emitting element, and the reflective member composition is arranged to expose the side surface of the light emitting element out of the fluorescent member and the reflective member.

9. The method for producing a light emitting device according to claim 1, wherein
the fluorescent member comprises
a first fluorescent member containing a fluorescent material having a reflectance at 405 nm in a range of 1% or more and 50% or less, wherein the fluorescent material is at least one fluorescent material selected from the group consisting of the first fluorescent material, the second fluorescent material, and the third fluorescent material, and
a second fluorescent member containing a fluorescent material having a higher reflectance at 405 nm than that of the fluorescent material contained in the first fluorescent member, the fluorescent material is at least one fluorescent material selected from the group consisting of the first fluorescent material, the second fluorescent material, and the third fluorescent material, and
the first fluorescent member is arranged on top of the light emitting element, and the second fluorescent member is arranged on the first fluorescent member.

10. The method for producing a light emitting device according to claim 9, wherein the first fluorescent member is arranged on top of a main surface of the light emitting element, and the second fluorescent member is arranged on the first fluorescent member.

11. The method for producing a light emitting device according to claim 7, wherein
the fluorescent member comprises
a first fluorescent member containing a fluorescent material having a reflectance at 405 nm in a range of 1% or more and 50% or less, wherein the fluorescent material is at least one fluorescent material selected from the group consisting of the first fluorescent material, the second fluorescent material, and the third fluorescent material, and
a second fluorescent member containing a fluorescent material having a higher reflectance at 405 nm than that of the fluorescent material contained in the first fluorescent member, the fluorescent material is at least one fluorescent material selected from the group consisting of the first fluorescent material, the second fluorescent material, and the third fluorescent material, and
the first fluorescent member is arranged on top of the light emitting element, and the second fluorescent member is arranged on the first fluorescent member and the reflective member, so as to cover a side surface of the light emitting element by the second fluorescent member.

12. The method for producing a light emitting device according to claim 9, wherein the first fluorescent member is arranged to cover top and a side surface of the light emitting element, and the second fluorescent member is arranged on the first fluorescent member.

13. The method for producing a light emitting device according to claim 9, wherein the first fluorescent member is arranged to cover a side surface of the light emitting element, and the second fluorescent member is arranged to cover top of the light emitting element and the first fluorescent member.

14. The method for producing a light emitting device according to claim 7, wherein the oxide contains at least one selected from the group consisting of yttrium, zirconium, aluminum, and titanium.

* * * * *